US009468465B2

(12) United States Patent
Weiner et al.

(10) Patent No.: US 9,468,465 B2
(45) Date of Patent: Oct. 18, 2016

(54) REVERSIBLE BONE COUPLING DEVICE AND METHOD

(71) Applicant: Nextremity Solutions, LLC, Colts Neck, NJ (US)

(72) Inventors: Lon S. Weiner, Rumson, NJ (US); Stuart D. Katchis, Scarsdale, NY (US); Arthur A. Alfaro, Colts Neck, NJ (US); Willem H. P. Van Iperen, Westfield, NJ (US); John R. Pepper, Cheshire, CT (US); Mari S. Truman, Warsaw, IN (US)

(73) Assignee: NEXTREMITY SOLUTIONS, INC., Warsaw, IN (US)

( * ) Notice: Subject to any disclaimer, the term of this patent is extended or adjusted under 35 U.S.C. 154(b) by 777 days.

(21) Appl. No.: 13/632,337

(22) Filed: Oct. 1, 2012

(65) Prior Publication Data
US 2013/0030475 A1 Jan. 31, 2013

Related U.S. Application Data

(63) Continuation-in-part of application No. 12/709,426, filed on Feb. 19, 2010, now Pat. No. 8,715,325.

(60) Provisional application No. 61/153,907, filed on Feb. 19, 2009.

(51) Int. Cl.
*A61B 17/04* (2006.01)
*A61B 17/86* (2006.01)
(Continued)

(52) U.S. Cl.
CPC ............ *A61B 17/68* (2013.01); *A61B 17/7291* (2013.01); *A61B 17/86* (2013.01);
(Continued)

(58) Field of Classification Search
CPC ................................ A61B 17/84; A61B 17/86
USPC .......................................................... 606/306
See application file for complete search history.

(56) References Cited

U.S. PATENT DOCUMENTS 3,991,425 A 11/1976 Martin et al.
4,246,662 A 1/1981 Pastrick
(Continued)

FOREIGN PATENT DOCUMENTS

EP 0831757 B1 11/2001
GB 1582974 A 1/1981
(Continued)

OTHER PUBLICATIONS

Caterini, et al., "Arthrodesis of the Toe Joints with an INtramedullary Cannulated Screw for Correction of Hammertoe Deformity," Foot & Ankle International, 2004, pp. 256-261, vol. 25, No. 4.
(Continued)

*Primary Examiner* — David Isabella
*Assistant Examiner* — Christine Nelson
(74) *Attorney, Agent, or Firm* — John W. Boger

(57) ABSTRACT

A reversible bone coupling device including a first component having a first elongated stem portion for insertion from a first end longitudinally into a surface of a first bone piece, and a second component having a second elongated stem portion for insertion from a second end longitudinally into a surface of a second bone piece, and a connector extending from a second top for coupling with the first component and reversibly locking therein.

22 Claims, 28 Drawing Sheets

(51) Int. Cl.
*A61F 2/08* (2006.01)
*A61B 17/68* (2006.01)
*A61F 2/30* (2006.01)
*A61F 2/42* (2006.01)
*A61B 17/72* (2006.01)

(52) U.S. Cl.
CPC ............... *A61F 2002/3085* (2013.01); *A61F 2002/30481* (2013.01); *A61F 2002/30487* (2013.01); *A61F 2002/30497* (2013.01); *A61F 2002/30622* (2013.01); *A61F 2002/423* (2013.01); *A61F 2002/4235* (2013.01)

(56) References Cited

U.S. PATENT DOCUMENTS

| | | |
|---|---|---|
| 4,304,011 A | 12/1981 | Whelan, III |
| D277,784 S | 2/1985 | Sgarlato et al. |
| 6,602,293 B1 | 7/1985 | Link et al. |
| 4,908,031 A | 3/1990 | Frisch |
| 5,037,440 A | 8/1991 | Koenig |
| 5,062,851 A | 11/1991 | Branemark |
| 5,129,903 A | 7/1992 | Luhr et al. |
| 5,167,661 A | 12/1992 | Wagenknecht |
| 5,207,712 A | 5/1993 | Cohen |
| 5,290,314 A | 3/1994 | Koch et al. |
| 5,417,692 A | 5/1995 | Goble et al. |
| 5,443,467 A | 8/1995 | Biedermann et al. |
| 5,683,466 A | 11/1997 | Vitale |
| 5,725,581 A | 3/1998 | Branemark |
| 5,810,591 A | 9/1998 | Huber |
| 5,810,822 A | 9/1998 | Mortier |
| 5,827,285 A | 10/1998 | Bramlet |
| 5,919,193 A | 7/1999 | Slavitt |
| 6,099,571 A | 8/2000 | Knapp |
| 6,284,001 B1 | 9/2001 | Knapp |
| 6,383,223 B1 | 5/2002 | Baehler et al. |
| 6,413,260 B1 | 7/2002 | Berrevoets et al. |
| 6,454,808 B1 | 9/2002 | Masada |
| 6,458,134 B1 | 10/2002 | Songer et al. |
| 6,517,543 B1 | 2/2003 | Berrevoets et al. |
| 6,852,113 B2 | 2/2005 | Nathanson et al. |
| 6,964,994 B1 | 11/2005 | Antonietti et al. |
| 7,041,106 B1 | 5/2006 | Carver et al. |
| 7,214,226 B2 | 5/2007 | Alleyne |
| 7,291,175 B1 | 11/2007 | Gordon |
| 7,297,165 B1 | 11/2007 | Kriek |
| 7,611,526 B2 | 11/2009 | Carl et al. |
| 7,635,364 B2 | 12/2009 | Barrall et al. |
| 7,837,738 B2 | 11/2010 | Reigstad et al. |
| 8,100,983 B2 | 1/2012 | Schulte |
| 8,303,589 B2 | 11/2012 | Tyber |
| 8,313,487 B2 | 11/2012 | Tyber |
| 8,328,806 B2 | 12/2012 | Tyber |
| 2004/0127900 A1 | 7/2004 | Konieczynski et al. |
| 2004/0220678 A1 | 11/2004 | Chow et al. |
| 2005/0043732 A1 | 2/2005 | Dalton |
| 2005/0113830 A1 | 5/2005 | Rezach et al. |
| 2005/0192587 A1 | 9/2005 | Lim |
| 2006/0052878 A1 | 3/2006 | Schmieding |
| 2006/0074492 A1 | 4/2006 | Frey |
| 2006/0195087 A1 | 8/2006 | Sacher et al. |
| 2008/0045963 A1 | 2/2008 | Abdou |
| 2008/0065224 A1 | 3/2008 | Reigstad et al. |
| 2008/0097611 A1 | 4/2008 | Mastrorio et al. |
| 2009/0157121 A1 | 6/2009 | Harris et al. |
| 2010/0036439 A1 | 2/2010 | Lavi |
| 2010/0121325 A1 | 5/2010 | Tyber |
| 2010/0256638 A1 | 10/2010 | Tyber |
| 2011/0054545 A1 | 3/2011 | Champagne |
| 2011/0082508 A1 | 4/2011 | Reed |
| 2011/0118739 A1 | 5/2011 | Tyber |
| 2011/0125153 A1 | 5/2011 | Tyber |

FOREIGN PATENT DOCUMENTS

| | | |
|---|---|---|
| GB | 2126097 A | 3/1984 |
| WO | 9309728 A1 | 5/1992 |
| WO | 9605784 A1 | 2/1996 |
| WO | 9716137 A1 | 5/1997 |
| WO | 2007109752 A2 | 9/2007 |

OTHER PUBLICATIONS

DE 19949890, Published Jun. 7, 2001, abstract only in English, downloaded from espacenet.com, 2 pages.
Edwards and Beischer, "Interphalangeal Join Arthrodesis of the Lesser Toes," Foot & Ankle Clinics North America, 2002, pp. 43-48, vol. 7.
Hetherington, "Metatarsalgia and Lesser Metatarsal Surgery," Hallux Valgus and Forefront Surgery textbook, 2000, pp. 429-451.
International Serch Report dated Jul. 9, 2010 in related PCT Appln. No. PCT/US10/024833, filed Feb. 19, 2010.
Iselin, et al. "Desarthodesis-Arthroplasties Interphalangiennes Proximales-" Conversion to Arthroplasty from Proximal Interphalangeal Joint Arthrodesis, Annales de Chirurgie de la Main, 1988, pp. 115-119, vol. 7, No. 2.
JP 2005073740, PUblished Mar. 24, 2005, abstract only in English, downloaded from espacenet.com, 1 page.
Konkel, et al., "Hammer Toe Correction Using an Absorbable Intramedullary Pin," Foot & Ankle International, 2007, pp. 916-920, vol. 28, No. 8.
Murray, "Surface Replacement Arthoplasty of the Proximal Interphalangeal Joint," The Journal of Hand Surgery, 2007, pp. 899-904, vol. 32A. No. 6.
SHIP Implant Brochure, Sgarlato Hammertoe Implant Procedure, Sgarlato Labs, Campbell, CA, 2006, 2 pages.
Sokolow, une prothese de (l'articulation interphlangienne prximale osteo-integree: IPP 2. Premier Resultsant- "Short Term Results of the IPP 2 Proximal Interphalangeal Joint Prosthesis," Chirgurgi de la Main, 2006, pp. 280-285, vol. 25, abstract only in English.

200
REVERSIBLE BONE COUPLING DEVICE AND METHOD

CROSS-REFERENCE TO RELATED APPLICATIONS

The present application is a continuation-in-part of U.S. Nonprovisional application Ser. No. 12/709,426 filed 19 Feb. 2010, which claims the benefit of U.S. Provisional Application Ser. No. 61/153,907 filed 19 Feb. 2009; which are incorporated herein by reference in their entireties.

TECHNICAL FIELD

The present disclosure relates to devices and methods for coupling bones with reversibly engaging bone coupling devices.

RELATED ART

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons. However, when the deformity is fixed, PIP fusion or joint replacement is often required. Implants available for this purpose include the Weil-Carver™ Hammertoe Implant (Biomet®, Inc., Warsaw, Ind.), Flexible Digital Implant (Tornier, Inc. Edina, Minn.), SHIP Implant (Sgarlato Labs, Campbell Calif.), Digital Compression Screw (BioPro®, Port Huron Mich.), Smart Toe™ Intramedullary Memory Implant (Memometal Inc., Memphis Tenn.), StayFuse™ Intramedullary Fusion Device (Tornier, Inc. Edina, Minn.), and Pro-Toe (Wright Medical, Arlington Tenn.). The latter three implants are used when fusion is desired, since the other implants allow some flexibility of the joint. With all current implants, placement is critical because, when mounted, there is no adjustability following initial implantation in the angle of flexion between the two cut bones to be coupled.

There is thus a need for alternative designs for implants for coupling two bone pieces, including implants that reversibly fix the two bone pieces. The present inventive concept addresses that need.

SUMMARY

These and other advantages of the present disclosure will be apparent to those of ordinary skill in the art by reference to the following Detailed Description and accompanying drawings/figures.

In an embodiment of the present disclosure, a reversible bone coupling device is disclosed. The reversible bone coupling device comprises a first component and a second component. The first component comprises a first elongated stem portion for insertion from a first end longitudinally into a surface of a first bone piece. The second component comprises a second elongated stem portion for insertion from a second end longitudinally into a surface of a second bone piece, and a connector extending from a second top for coupling with the first component and locking therein. The first component includes a reversibly engaging locking mechanism for disengaging the connector from the first component.

In another embodiment, the reversibly engaging locking mechanism supports incremental locking of the connector of the second component with the first component.

In another embodiment, the reversibly engaging locking mechanism supports disengagement of the connector of the second component from the first component.

In another embodiment, the connector comprises a plurality of grooves, each groove adapted for interlocking with the first component.

In another embodiment, the device promotes fusion of the first bone piece to the second bone piece.

In another embodiment, the first elongated stem portion of the first component comprises a cavity that extends within the first elongated stem from a first top toward the first end, the cavity capable of receiving the connector of the second component.

In another embodiment, the reversibly engaging locking mechanism comprises an integral tab for mating with any of a plurality of grooves of the connector.

In another embodiment, the reversibly engaging locking mechanism comprises an integral deflection means.

In another embodiment, the integral deflection means is at least one of an integral tab and an inline deformed tab.

In another embodiment, the first elongated stem portion of the first component comprises an opening and an internal lock ring, the opening capable of receiving the connector of the second component.

In another embodiment, the connector comprises a plurality of notches for mating with the internal lock ring of the first elongated stem portion.

In another embodiment, the internal lock ring comprises a plurality of bosses for anchoring the internal lock ring in the first component to prevent rotation.

In another embodiment, the first elongated stem portion further comprises a cavity defined by a wall, a closed distal end, and an open proximal end, and the cavity receives the connector.

In another embodiment, the connector is capable of being adjustably positioned in relation to the second top when coupling with the first component.

In another embodiment, each of the first elongated stem portion and the second elongated stem portion are at least one of cylindrical and conical.

In another embodiment, at least one of the first elongated stem portion and the second elongated stem portion is a spiraling thread.

In another embodiment, the spiraling thread is a continuous spiraling thread.

Additional aspects, advantages, and utilities of the present disclosure will be set forth in part in the description which follows and, in part, will be obvious from the description, or may be learned by practice of the embodiments of the present disclosure.

DETAILED DESCRIPTION

Figure 1:
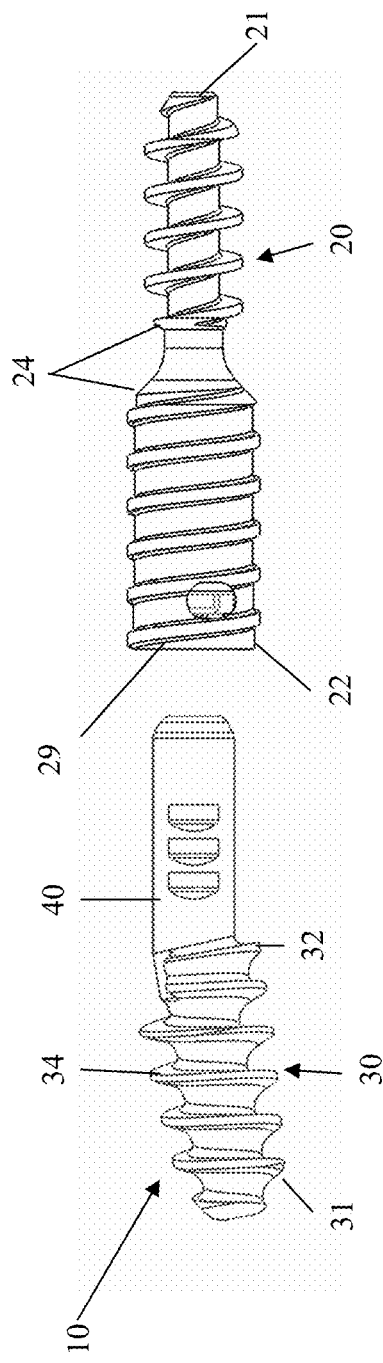
FIG. 1 illustrates a bone fusion device in accordance with an embodiment of the present disclosure.

The present disclosure relates to devices and methods for coupling bones with reversibly engaging bone coupling devices. In some embodiments, a reversible bone coupling device facilitates adjustment of an angle between two bones to be coupled, as well as being reversibly engaging to assist in corrections of the coupling of the two bones.

The reversible bone coupling device comprises a first component and a second component. The first component comprises a first elongated stem portion comprising a first end and a first top opposite the first end. The first elongated stem portion is suitable for insertion from the first end longitudinally into a surface of a first bone piece of a bone. The second component comprises a second elongated stem portion comprising a second end and a second top. The second elongated stem portion is suitable for insertion from the second end longitudinally into a surface of a second bone piece of the bone. The second component further comprises a connector extending from the second top. The connector is capable of coupling with the first component and locking therewith to couple the first component and the second component. The first component further comprises a reversibly engaging locking mechanism that locks the connector, and facilitates unlocking of the connector to allow adjustment of the fusion between the first component and the second component.

In certain embodiments, the first component is a female component and the second component is a male component. The first elongated stem portion of the female component may comprise an opening that extends axially from the first top toward the first end. The connector may comprise an elongated shaft, a proximal end, a top of shaft near the proximal end, and a distal end, where the connector is capable of insertion into the opening in the first elongated stem portion and locking therein to couple the male component and the female component.

The device is useful for coupling any two bone pieces, and by way of the reversibly engaging mechanism, the connector may be reversed to adjust the position of the connector or remove the connector entirely in situations where adjustment of the device may be necessary or contemplated to further assist in coupling or fusing cut surfaces of bones. As a result, the device is adaptable to any bone size, shape, or configuration of any patient. In some embodiments, the device is particularly useful in coupling or fusing cut surfaces of bones such as cut ends of fingers or toes. This may facilitate the treatment of hammertoe, claw toe, mallet toe, or curly toe. In these embodiments, the first elongated stem portion is suitable for insertion from the first end longitudinally into a cut surface of a resected phalanx, metatarsal or metacarpal, or a cut diaphyhsis, and the second elongated stem portion is suitable for insertion from the second end longitudinally into a cut surface of a resected phalanx, metatarsal or metacarpal, or a cut diaphyhsis.

In the various embodiments described herein and corresponding with the Figures provided herewith, a bone fixation or fusion method and system are described. A first component of a bone fusion device is inserted into a first bone piece. A second component of a bone fusion device is inserted into a second bone piece. A connector of the second component is inserted into a cavity of the first component. The connector is locked within the cavity of the first component by a reversibly engaging locking mechanism to facilitate formation of a fused bone. If necessary, the reversibly engaging locking mechanism may be adjusted to allow the connector and corresponding second component to be longitudinally adjusted or removed from the first component to facilitate adjustments or modifications during or after surgery.

FIG. 1 illustrates a bone fusion device in accordance with an embodiment of the present disclosure. Bone fusion device 10 includes a female component 20 and a male component 30. Female component 20 is an elongated stem comprising a first end 21, a first top 22, and a cavity 29. Female component 20 also includes a spiraling thread 24 on the exterior, suitable for screwing female component 20 into a bone or bone piece.

Male component 30 is an elongated stem comprising a second end 31 and a second top 32. Male component 30 further includes a connector 40 extending from the second top 32. In certain embodiments, connector 40 may be configured to be adjustably attached to the elongated stem of the male component 30, thus supporting the effective lengthening or shortening of the male component 30. Male component 30 also includes a spiraling thread 34 on the exterior, suitable for screwing male component 30 into a bone or bone piece.

Female component 20 and male component 30 can independently be cylindrical or conical, or any combination thereof. Where the illustrated embodiments show spiraling threads as means to anchor a male component or female component to a bone, alternate anchoring means may be used. Where present, the spiraling threads can be of any type known in the art for screwing into a bone. Thus, in some embodiments, the spiraling thread is a continuous spiraling thread. In other embodiments, the spiraling thread allows self-tapping and/or self-threading.

In an embodiment, the spiraling threads may be continuous. In yet another embodiment, the spiraling threads may spiral in the same direction so that when the device is screwed into opposing bone surfaces and coupled, the opposing pitch of the threads in the bone prevents the device from unscrewing.

The embodiments described herein are not limited to any particular pitch of one rotation of the continuous spiraling thread. For example, the pitch may be 5 mm or greater, 4 mm, 3 mm, 2 mm, 1 mm, or any distance in between the aforementioned distances.

Figure 6:
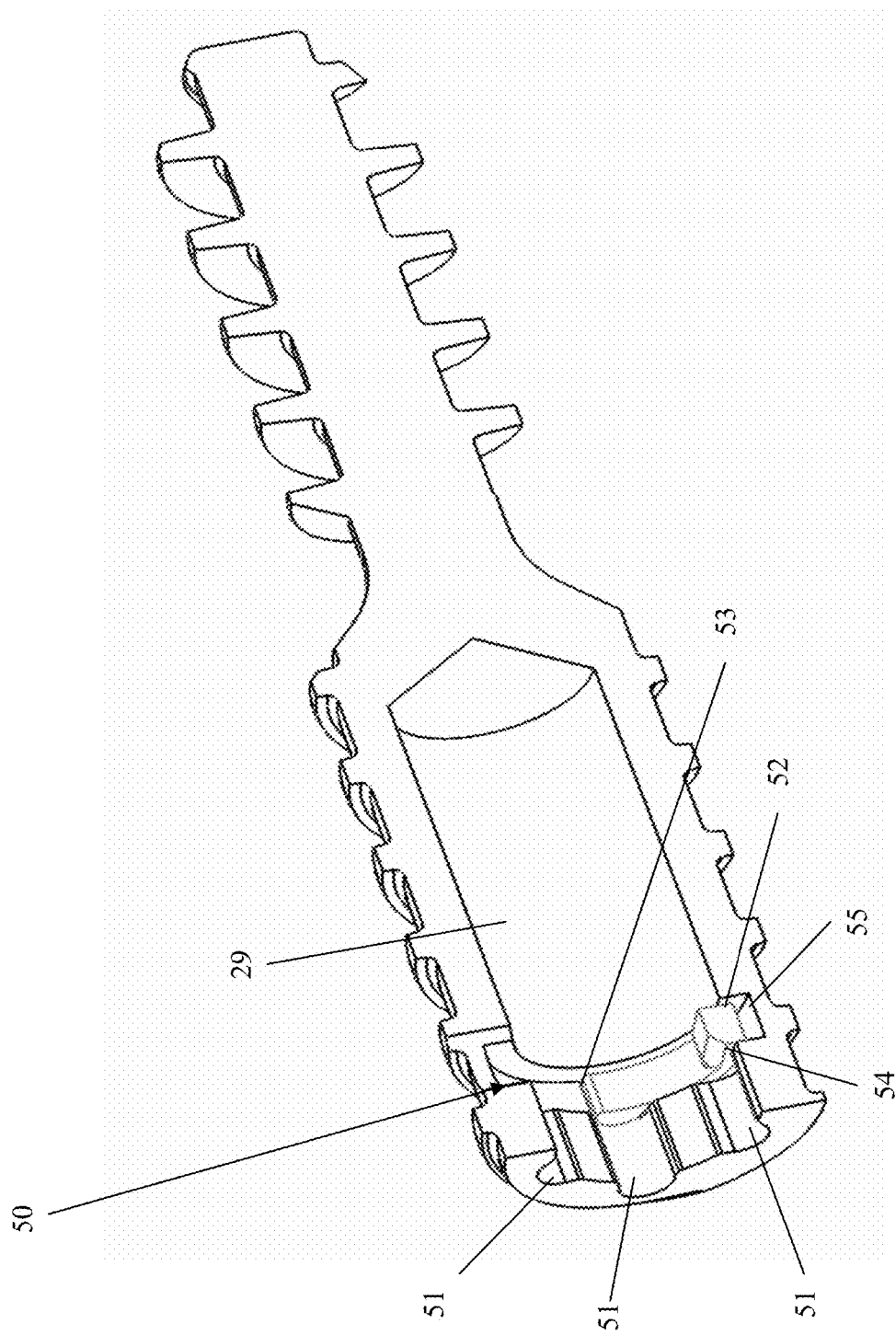
FIG. 6 illustrates a perspective and cut-away view of a female component of a bone fusion device in accordance with an embodiment of the present disclosure.

Connector 40, as shown in FIG. 1, may comprise grooves for interlocking with a reversibly engaging locking mechanism of female component 20. When a particular groove engages reversibly engaging locking mechanism 50 (as shown in FIG. 6), reversibly engaging locking mechanism locks the connector of the male component within the female component such that the bone pieces that the male component and the female component are screwed into become coupled or fused as a bone fusion.

Figure 2:
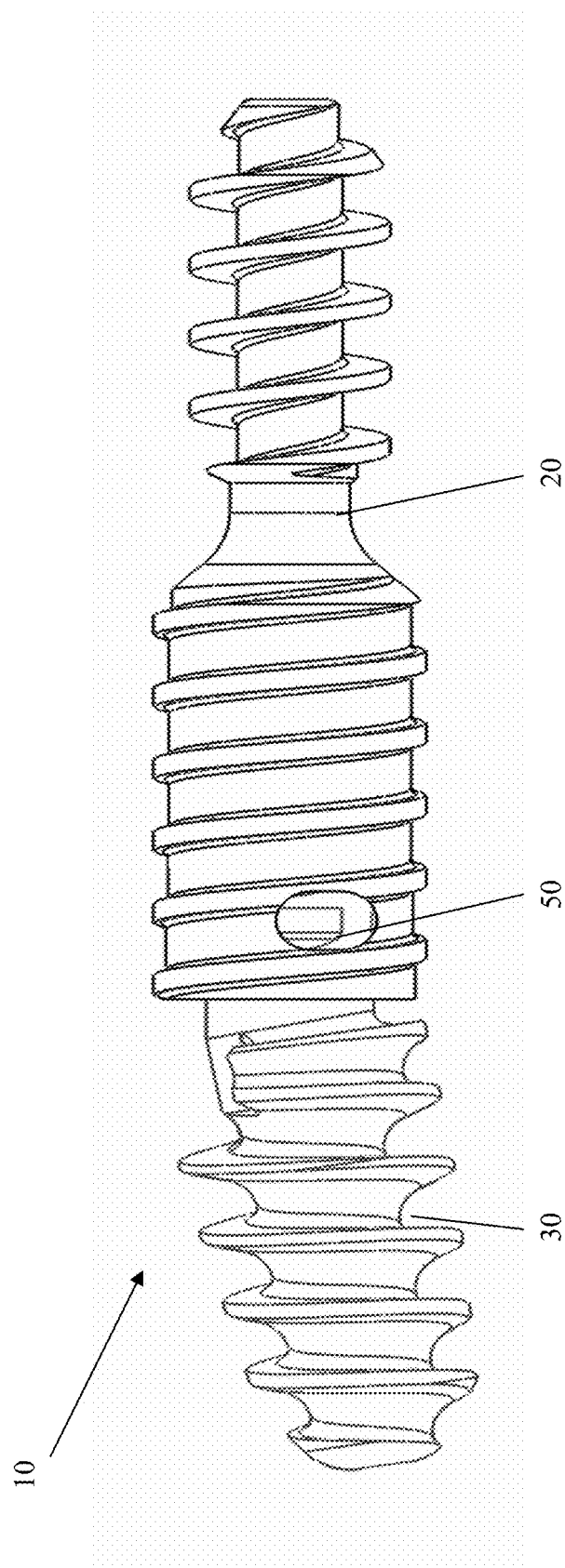
FIG. 2 illustrates a bone fusion device after fusion of the male and female component in accordance with an embodiment of the present disclosure.

FIG. 2 illustrates a bone fusion device after coupling of the male and female component in accordance with an embodiment of the present disclosure. FIG. 2 shows bone fusion device 10 after connector 40 of male component 30 has been inserted into cavity 29 of female component 20. When bone fusion device 10 is in the state as depicted, the bones that male component 30 and female component 20 have been screwed into are effectively coupled or fused together. Connector 40 is held and locked within the female component by the reversibly engaging locking mechanism 50.

Figure 3:
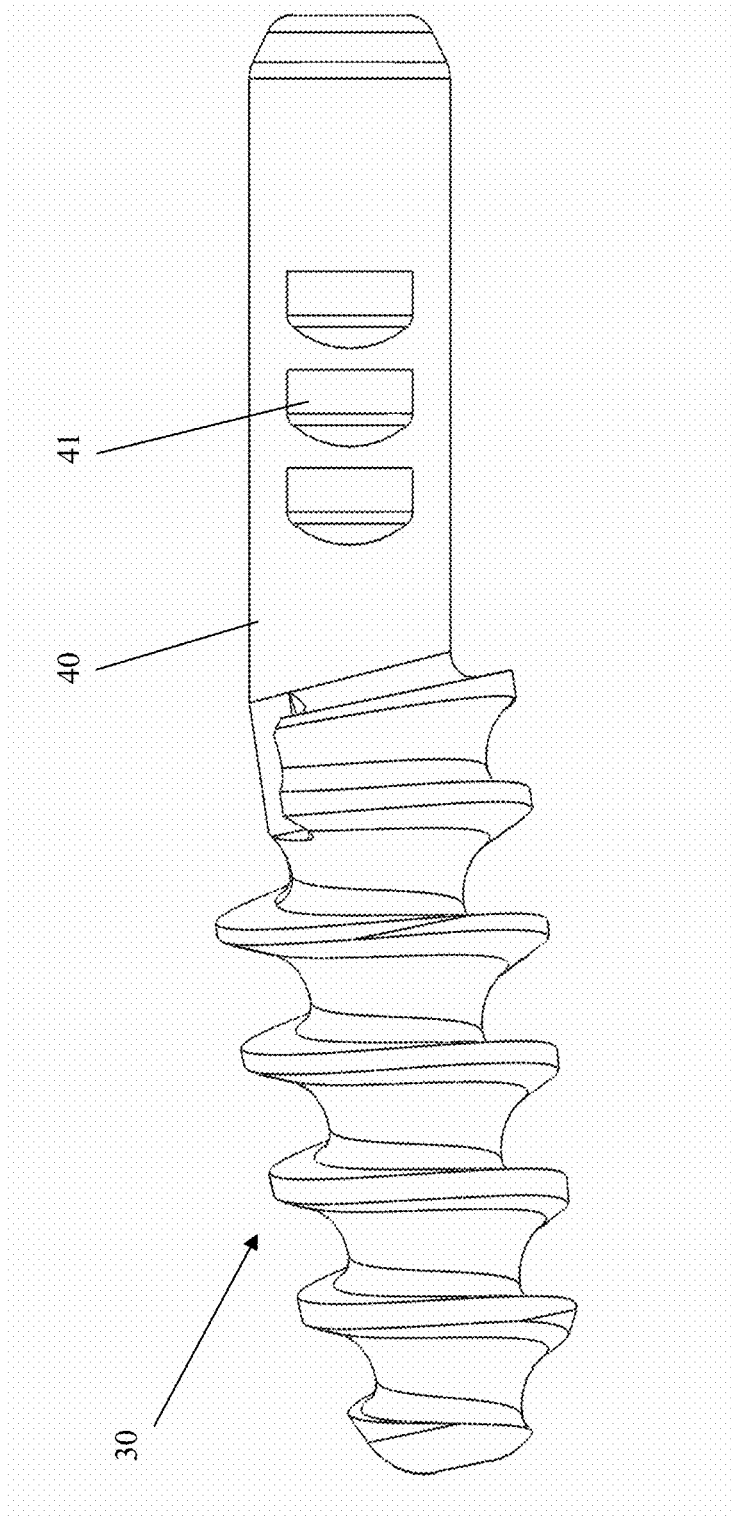
FIG. 3 illustrates a side view of a male component of a bone fusion device in accordance with an embodiment of the present disclosure.

FIG. 3 illustrates a side view of a male component of a bone fusion device in accordance with an embodiment of the present disclosure. Male component 30, as shown, includes connector 40, which comprises a plurality of grooves 41 for engaging with a reversibly engaging locking mechanism to lock connector 40 within a female component to couple the male component and the female component.

Figure 4:
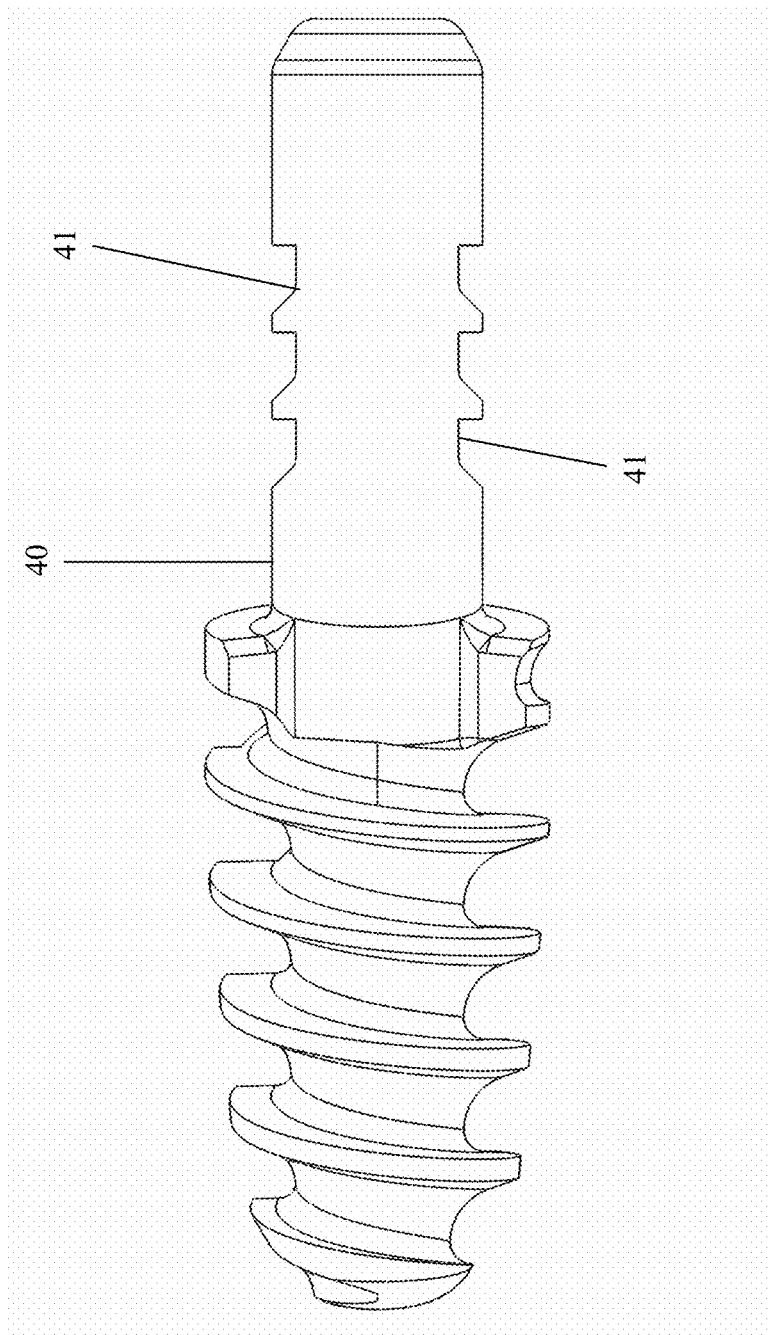
FIG. 4 illustrates another side view of a male component of a bone fusion device in accordance with an embodiment of the present disclosure.

FIG. 4 illustrates another side view of a male component of a bone fusion device in accordance with an embodiment of the present disclosure. The plurality of grooves 41, as shown in FIG. 4, may be on two sides of connector 40.

Figure 5:
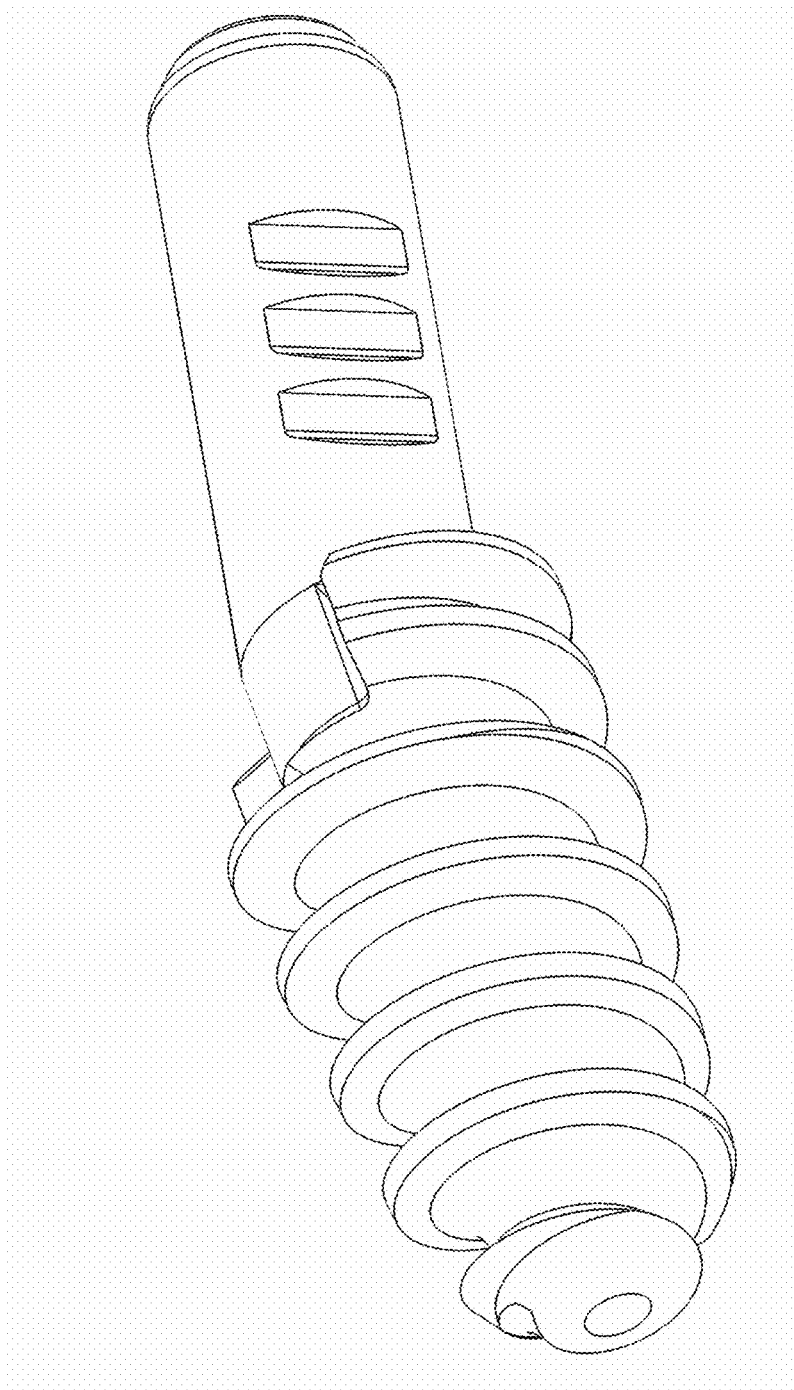
FIG. 5 illustrates a perspective view of a male component of a bone fusion device in accordance with an embodiment of the present disclosure.

FIG. 5 illustrates a perspective view of a male component of a bone fusion device in accordance with an embodiment of the present disclosure.

FIG. 6 illustrates a perspective and cut-away view of a female component of a bone fusion device in accordance with an embodiment of the present disclosure. In the cross-section view, the inside of cavity 29 is viewable. Within cavity 29 are a plurality of lobes 51 and a ring 52, both of which are a part of reversibly engaging locking mechanism 50. Ring 52 rests within a slot 55 that is sized for receiving ring 52. In an embodiment, the plurality of lobes 51 is located at the opening of cavity 29. The plurality of lobes 51 are configured such that any one or two of the lobes may receive a corresponding boss 53 of ring 52 to prevent rotation of ring 52. As FIG. 6 illustrates a cut-away view, only three lobes 51 are viewable and one boss 53 of ring 52. Additionally, a portion of a chamfer 54 of ring 52 is viewable. Chamfer 54 protrudes so that when connector 40 is inserted into cavity 29, chamfer 54 engages with any of grooves 41 to lock connector 40 within female component 20. Ring 52 allows rotational unlocking of connector 40 from female component 20. Ring 52 may be rotated to unlock chamfer 54 from a groove of connector 40, and allow connector 40 to be pulled outwards from cavity 29. This facilitates complete removal of connector 40 from cavity 29 or adjustment such that a different groove of connector 40 can be caused to engage with chamfer 54 to lock connector 40 within female component 20 in a new position.

Figure 7:
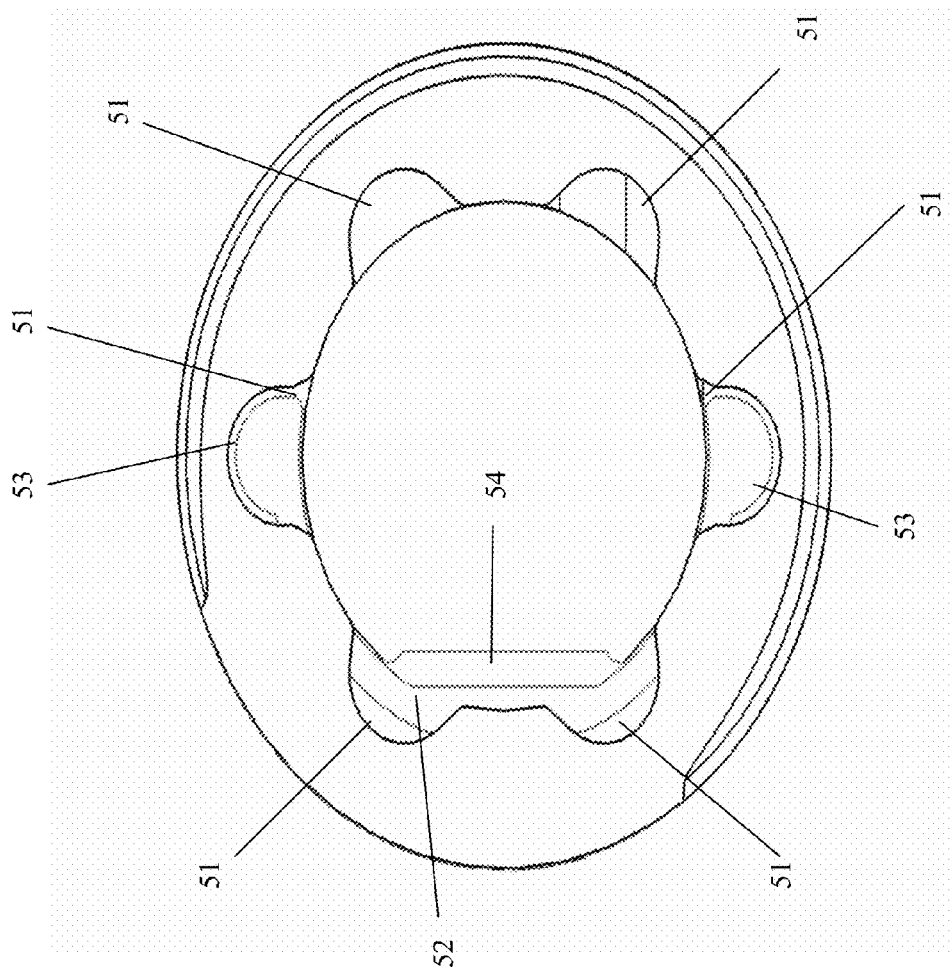
FIG. 7 illustrates a view of the opening of a cavity of a female component of a bone fusion device in accordance with an embodiment of the present disclosure.

FIG. 7 illustrates a view of the opening of a cavity of a female component of a bone fusion device looking from the first end 21 toward the first top 22, in accordance with an embodiment of the present disclosure. Cavity 29, as shown, includes six lobes 51, and ring 52 which rests within a slot within the cavity. Ring 52 includes two bosses 53, each of which is engaged with a corresponding lobe 51 to hold ring 52 in place within cavity 29. More specifically, lobes 51 anchor bosses 53 of a ring 52 to prevent rotation of ring 52. Chamfer 54, shown in FIG. 7, protrudes from ring 52 in order to engage with grooves of a connector. The cavity may include any number of lobes depending on the size of the lobes and the cavity, provided that the lobes of sufficient size to secure two or more bosses to prevent rotation of the ring. The ring may have two or more bosses provided that they are of sufficient size to remain secured in the lobes so as to prevent rotation of the ring.

Figure 8A:
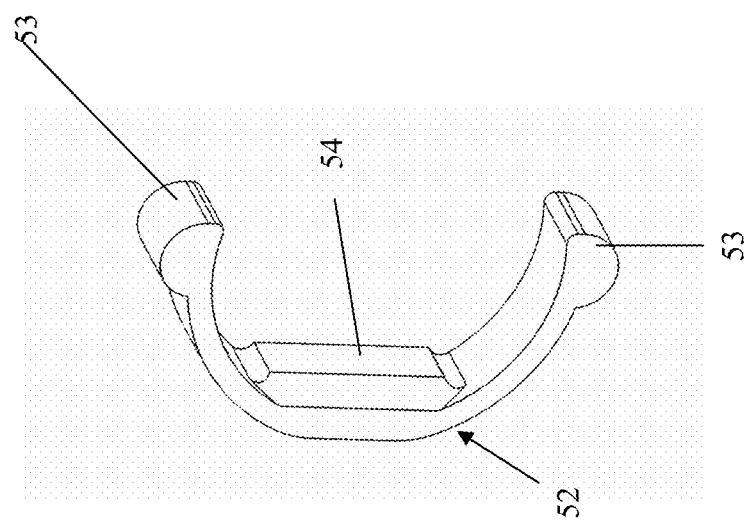
FIGS. 8a-c illustrate perspective views of a ring of a reversibly engaging locking mechanism of a bone fusion device in accordance with an embodiment of the present disclosure.
Figure 8B:
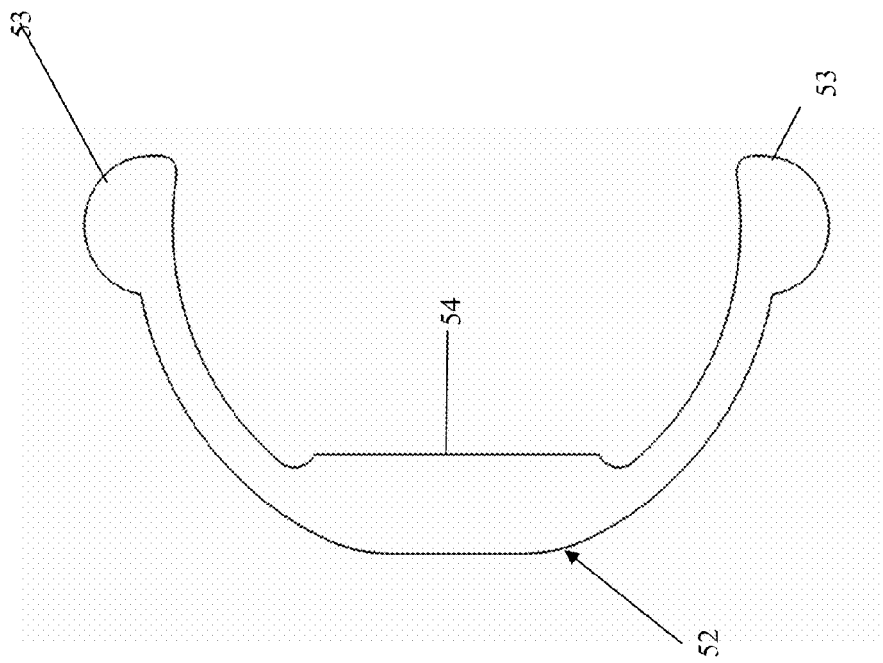
Figure 8C:
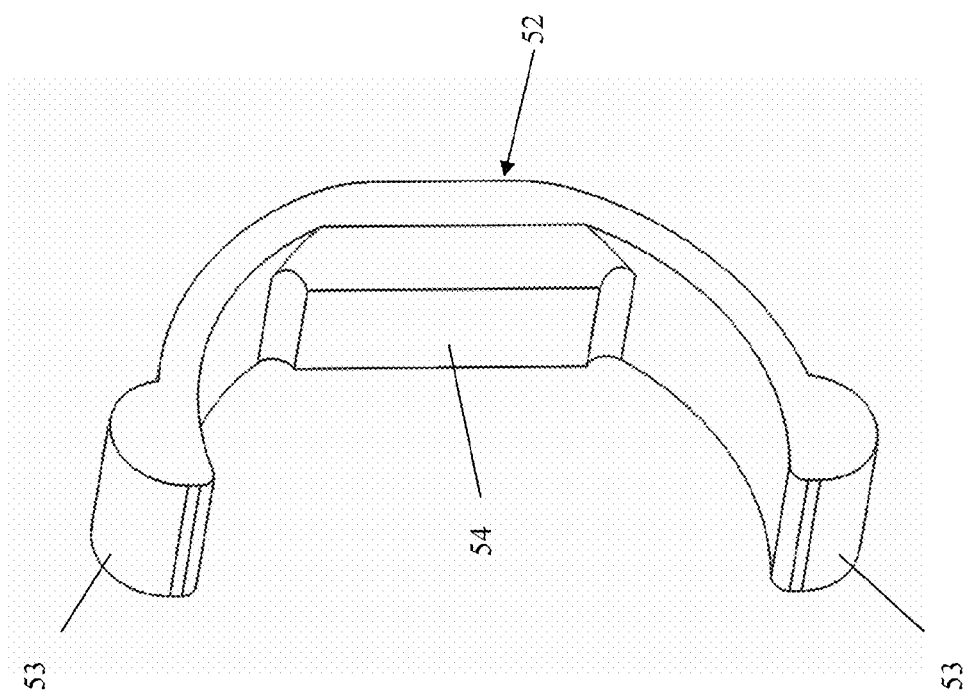

FIGS. 8a-c illustrate perspective views of a ring of a reversibly engaging locking mechanism of a bone fusion device in accordance with an embodiment of the present disclosure.

Figure 9:
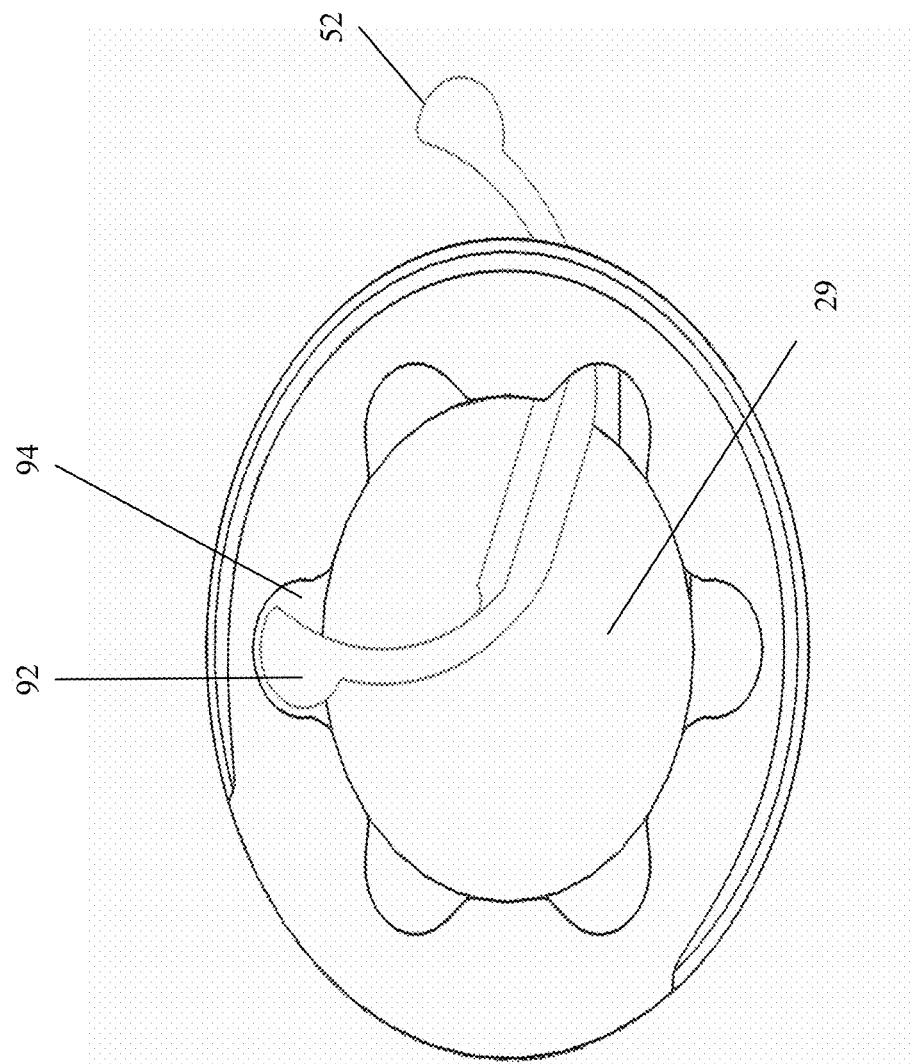
FIG. 9 illustrates a view of the opening of a cavity of a female component of a bone fusion device with a partially disengaged ring of a reversibly engaging locking mechanism in accordance with an embodiment of the present disclosure.

FIG. 9 illustrates a view of the opening of a cavity 29 of a female component of a bone fusion device with a partially disengaged ring 52 of a reversibly engaging locking mechanism in accordance with an embodiment of the present disclosure. Ring 52 as shown is partially disengaged since only one boss 92 is currently engaged with a lobe 94. FIG. 9 is meant to illustrate how ring 52 is inserted into cavity 29. Ring 52 is inserted into cavity 29 through an opening (not shown) on a side of female component 20. Once one end of ring 52 is inserted, a boss, such as boss 92 of that end may be engaged with a lobe 94.

Figure 10:
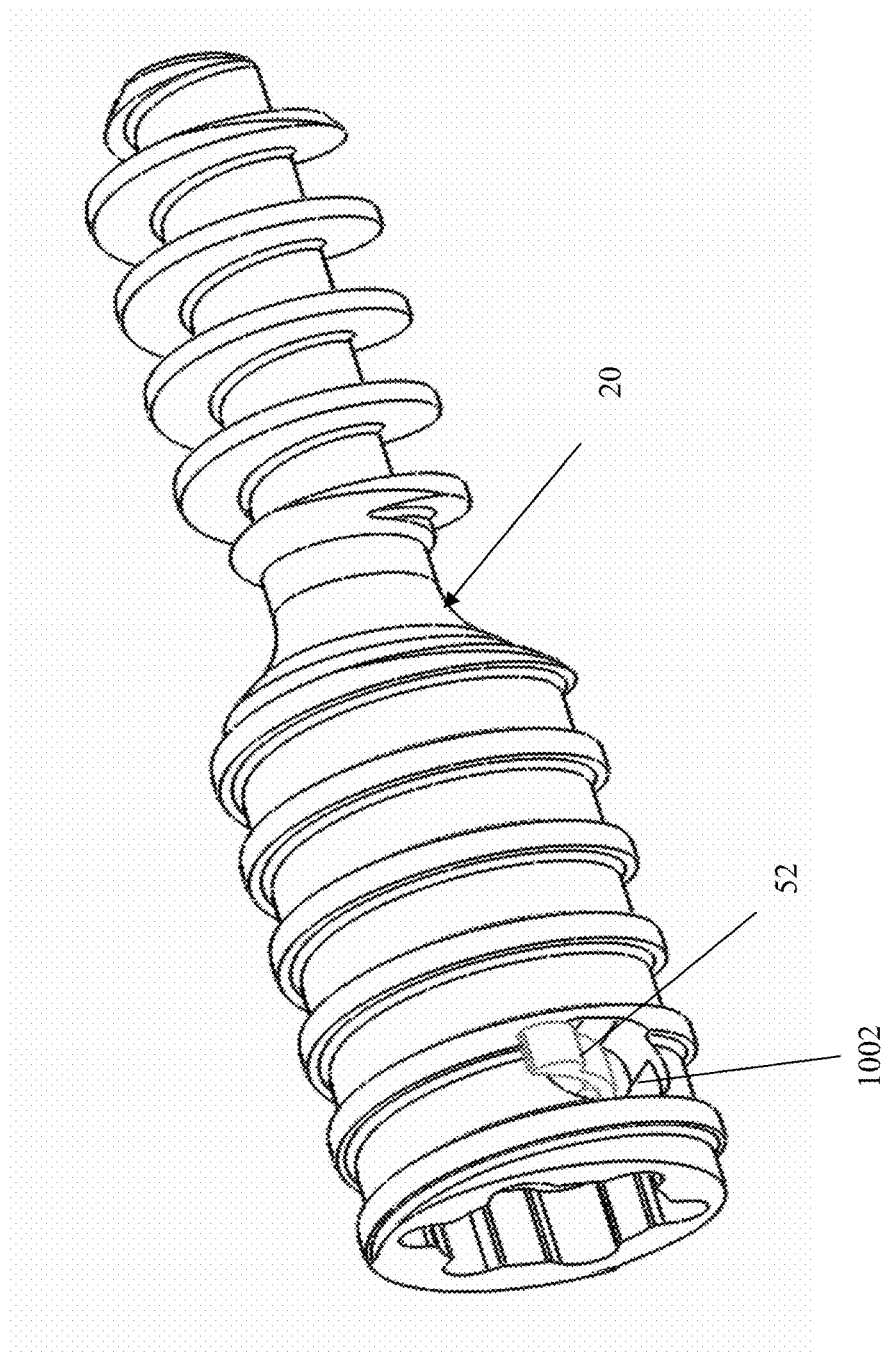
FIG. 10 illustrates a perspective view of a female component of a bone fusion device including an opening for receiving a ring of a reversibly engaging locking mechanism.

FIG. 10 illustrates a perspective view of a female component of a bone fusion device including an opening for receiving a ring of a reversibly engaging locking mechanism. FIG. 10 shows an opening 1002 of female component 20 for receiving ring 52.

Figure 11:
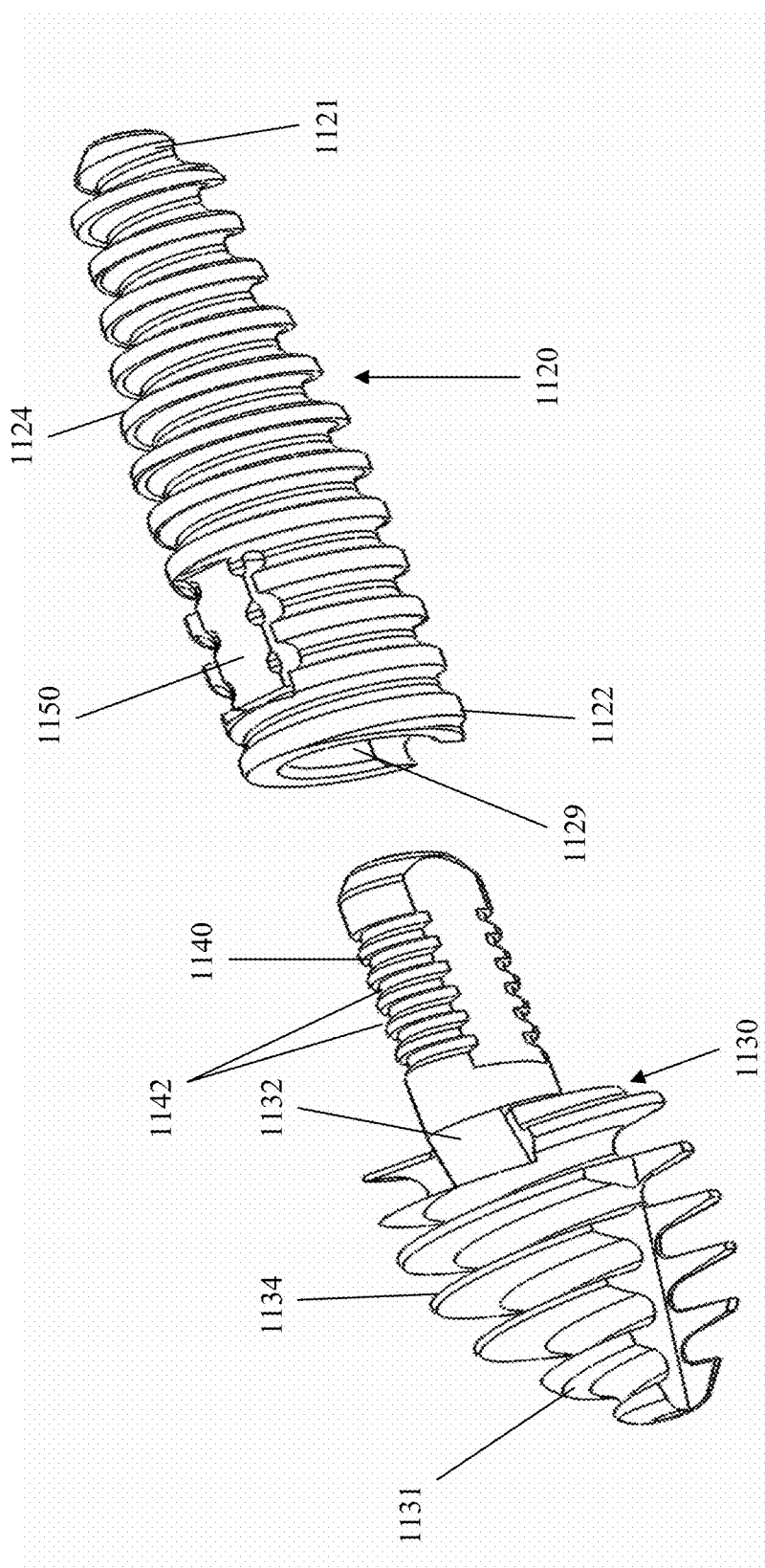
FIG. 11 illustrates a bone fusion device in accordance with an embodiment of the present disclosure.

FIG. 11 illustrates a bone fusion device in accordance with an embodiment of the present disclosure. Bone fusion device 1110 includes a female component 1120 and a male component 1130. Female component 1120 is an elongated stem comprising a first end 1121, a first top 1122, and a cavity 1129. Female component 1120 also includes a spiraling thread 1124 on the exterior, suitable for screwing female component 1120 into a bone or bone piece.

Male component 1130 is an elongated stem comprising a second end 1131 and a second top 1132. Male component 1130 further includes a connector 1140 extending from second top 1132. Male component 1130 also includes a spiraling thread 1134 on the exterior, suitable for screwing male component 1130 into a bone or bone piece.

Female component 1120 and male component 1130 can independently be cylindrical or conical, or any combination thereof. Where the illustrated embodiments show spiraling threads as means to anchor a male component or female component to a bone, alternate anchoring means may be used. Where present, the spiraling threads can be of any type known in the art for screwing into a bone. Thus, in some embodiments, the spiraling thread is a continuous spiraling thread. In other embodiments, the spiraling thread allows self-tapping and/or self-threading.

In an embodiment, the spiraling threads may be continuous. In yet another embodiment, the spiraling threads may spiral in the same direction so that when the device is screwed into opposing bone surfaces and coupled, the opposing pitch of the threads in the bone prevents the device from unscrewing.

The embodiments described herein are not limited to any particular pitch of one rotation of the continuous spiraling thread. For example, the pitch may be 5 mm or greater, 4 mm, 3 mm, 2 mm, 1 mm, or any distance in between the aforementioned distances.

Connector 1140, as shown in FIG. 11, may comprise grooves 1142 for interlocking with a reversibly engaging locking mechanism 1150 of female component 1120. When a particular groove 1142 engages reversibly engaging locking mechanism 1150, reversibly engaging locking mechanism 1150 locks the connector of the male component within the female component such that the bone pieces that the male component and the female component are screwed into become coupled or fused as a bone fusion. Reversibly engaging locking mechanism 1150 may be an integral deflection means such as an integral tab that has been cut into a wall of female component 1120. The integral tab may be deflected inward or be a machined tab protruding inside the main diameter of cavity 1129. The integral tab fits within grooves of connector 1140 in order to lock connector 1140 in place within female component 1120. Axial force applied to the integral tab will unlock the integral tab from a groove of connector 1140. For example, integral tab may be bent inwards or outwards at a specific angle to release connector 1140. Once released, connector 1140 may be adjusted within cavity 1129 of female component 1120, or connector 1140 may be removed entirely.

Figure 12:
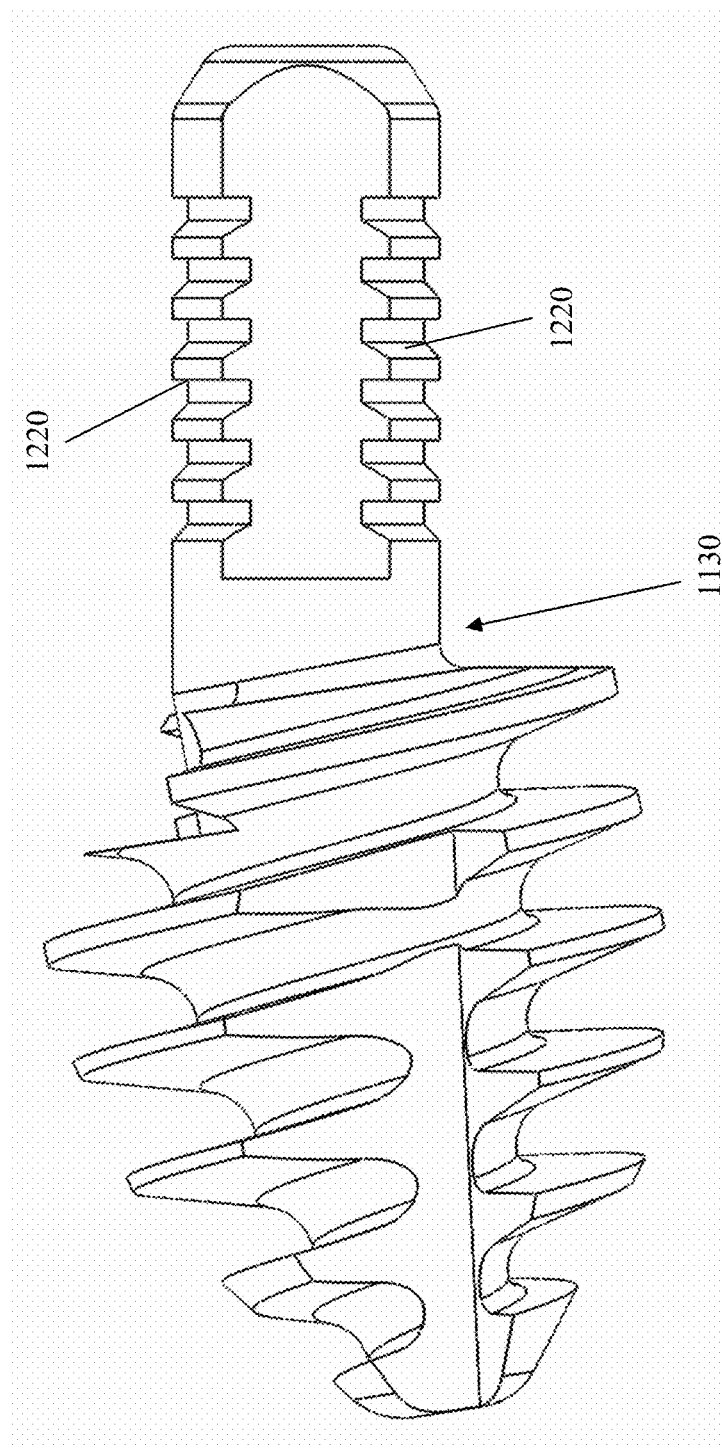
FIG. 12 illustrates a male component of a bone fusion device in accordance with an embodiment of the present disclosure.

FIG. 12 illustrates a male component of a bone fusion device in accordance with an embodiment of the present disclosure. Male component 1130, as shown, includes a plurality of grooves 1220. The plurality of grooves 1220 are configured as segmental recesses, which support rotational unlocking of connector 1140 from reversibly engaging locking mechanism 1150 which comprises an integral tab.

Figure 13:
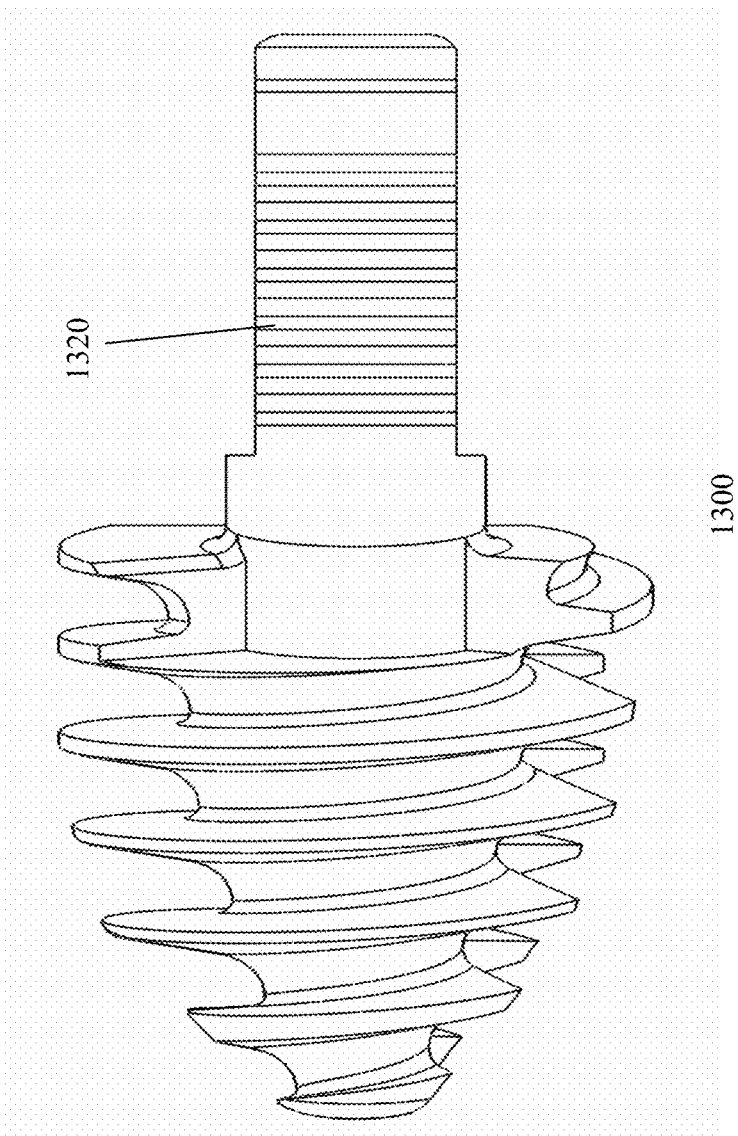
FIG. 13 illustrates another male component of a bone fusion device in accordance with an embodiment of the present disclosure.

FIG. 13 illustrates another male component of a bone fusion device in accordance with an embodiment of the present disclosure. Male component 1300 includes a plurality of grooves 1320. The plurality of grooves 1320 are full radial grooves that may lock with an integral tab of reversibly engaging locking mechanism, and unlock when axial force is applied to reversibly engaging locking mechanism.

Figure 14:
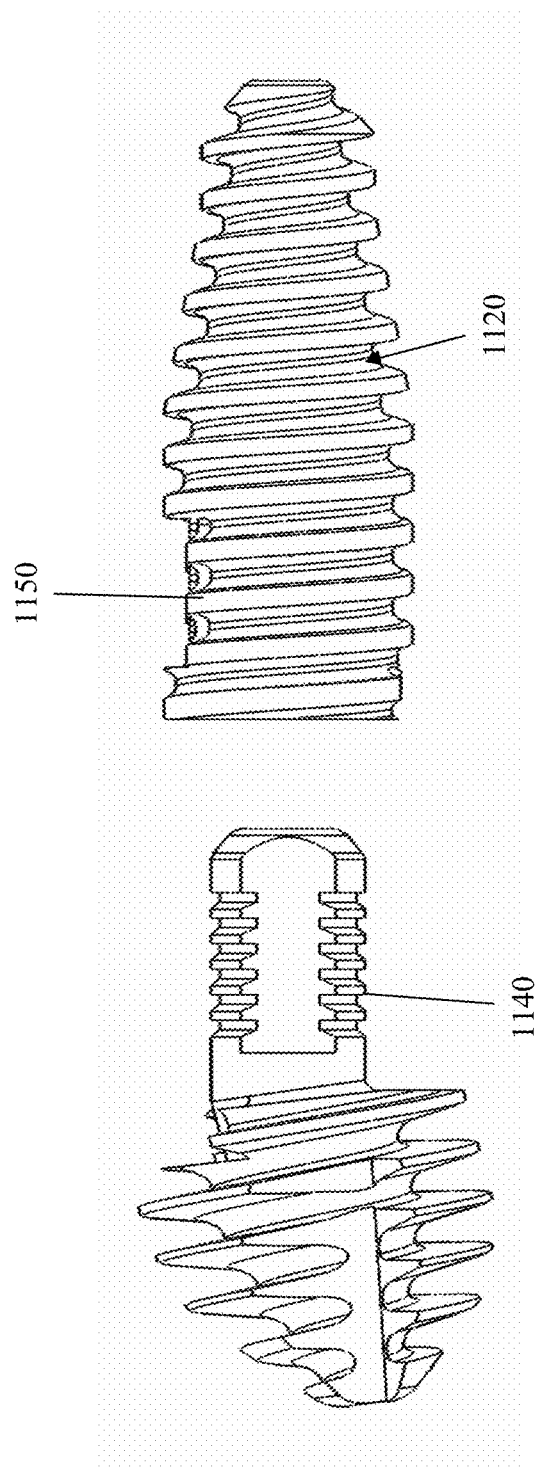
FIG. 14 illustrates a female component of a bone fusion device in accordance with an embodiment of the present disclosure.

FIG. 14 illustrates a female component of a bone fusion device in accordance with an embodiment of the present disclosure. Female component 1120, is shown. On a wall of female component 1120, is an integral tab of reversibly engaging locking mechanism 1150, which has been cut into the wall of female component 1120.

Figure 15:
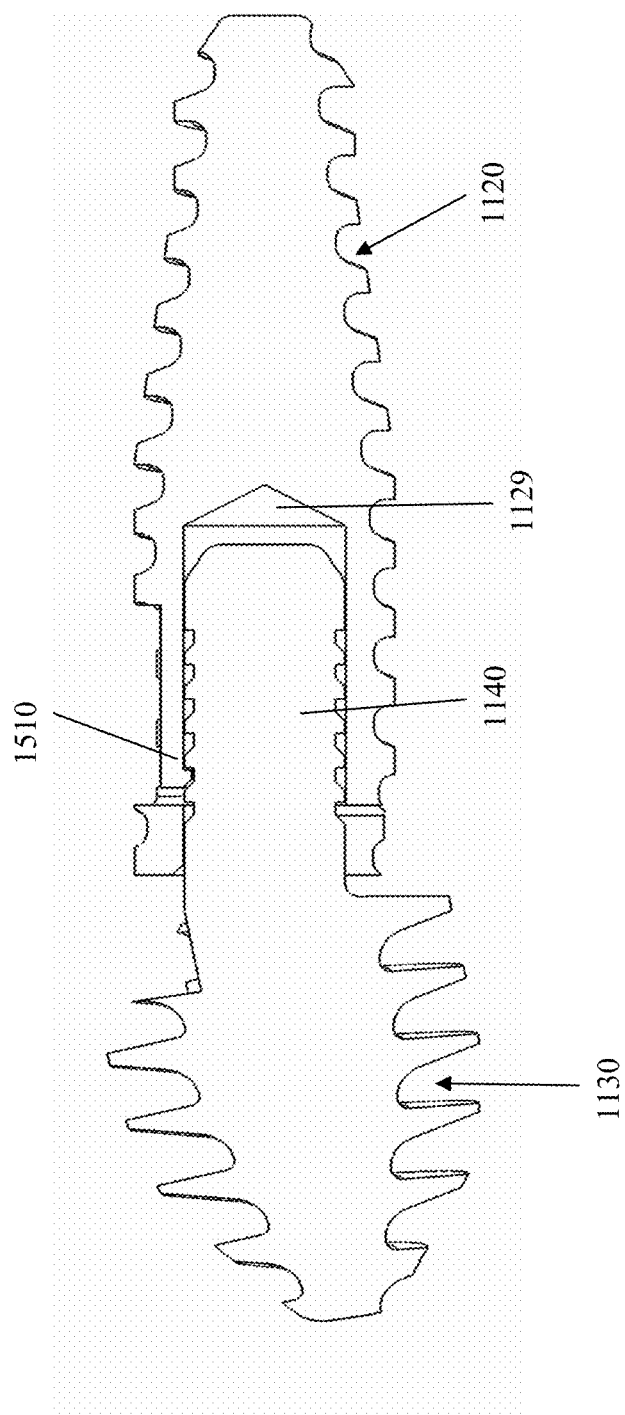
FIG. 15 illustrates a cross-sectional view of a bone fusion device after coupling of a female component and a male component in accordance with an embodiment of the present disclosure.

FIG. 15 illustrates a cross-sectional view of a bone fusion device after coupling of a female component and a male component in accordance with an embodiment of the present disclosure. Connector 1140 of male component 1130 has been inserted into cavity 1129 of female component 1120. Connector 1140 is held in place by integral tab 1510 of the reversibly engaging locking mechanism. Integral tab 1510 may be deflected inwards or protrude inside the main diameter of the cavity 1129. Application of axial force to integral tab 1510 facilitates unlocking of integral tab 1510 from a groove of connector 1140 to allow for adjustment of connector 1140 within cavity 1129.

Figure 16:
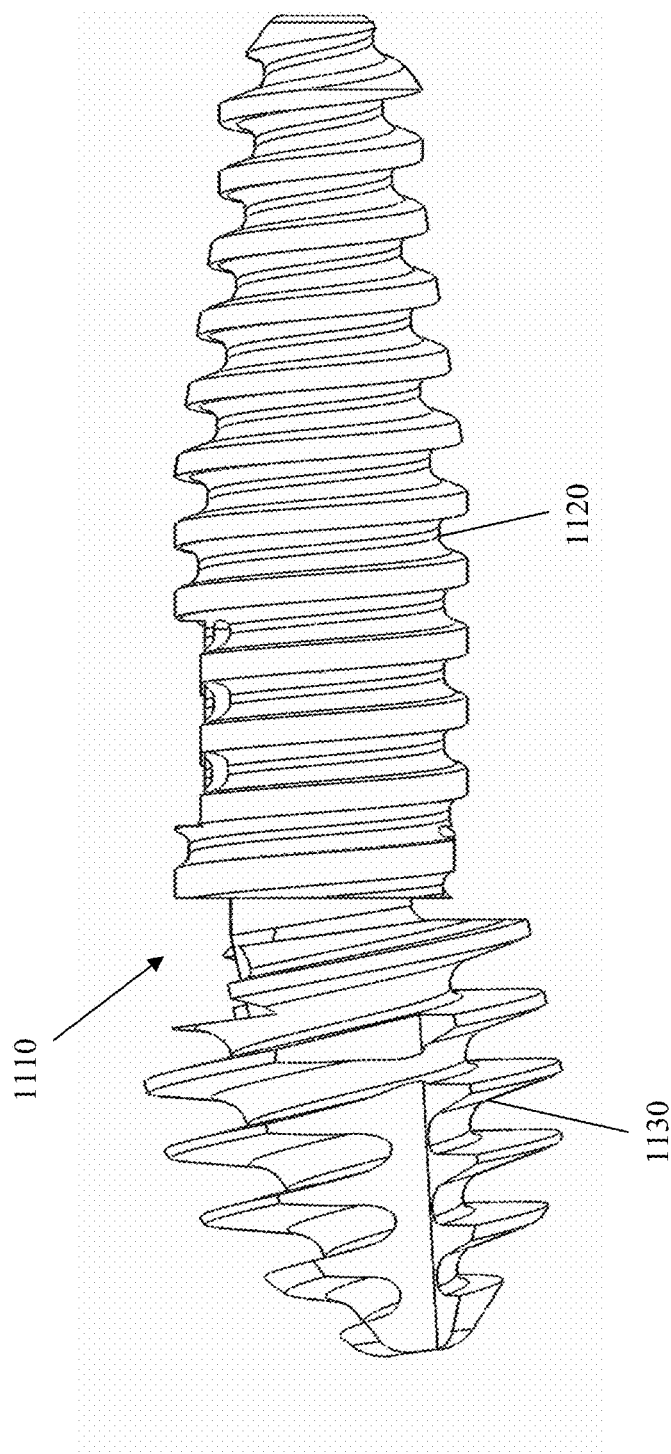
FIG. 16 illustrates a bone fusion device after fusion of a female component and a male component in accordance with an embodiment of the present disclosure.

FIG. 16 illustrates a bone fusion device after coupling of a female component and a male component in accordance with an embodiment of the present disclosure. Bone fusion device 1110 is shown by FIG. 16 in a position where both female component 1120 and male component 1130 are coupled.

Figure 17:
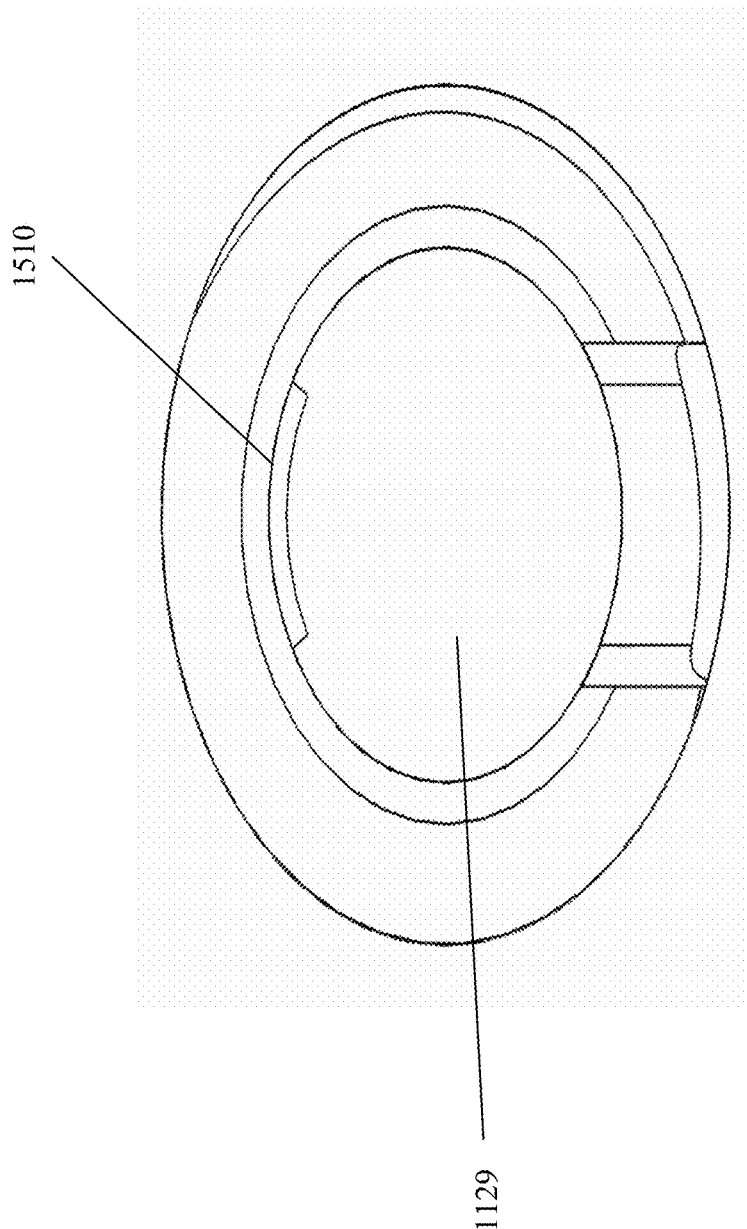
FIG. 17 illustrates a view into a cavity of a female component of a bone fusion device in accordance with an embodiment of the present disclosure.

FIG. 17 illustrates a view into a cavity of a female component of a bone fusion device in accordance with an embodiment of the present disclosure. In the view into cavity 1129 provided by FIG. 17, a portion of integral tab 1510 is visible. This portion of integral tab 1510 of the reversibly engaging locking mechanism is a portion that engages with a groove of the connector to lock the connector in place within cavity 1129.

Figure 18:
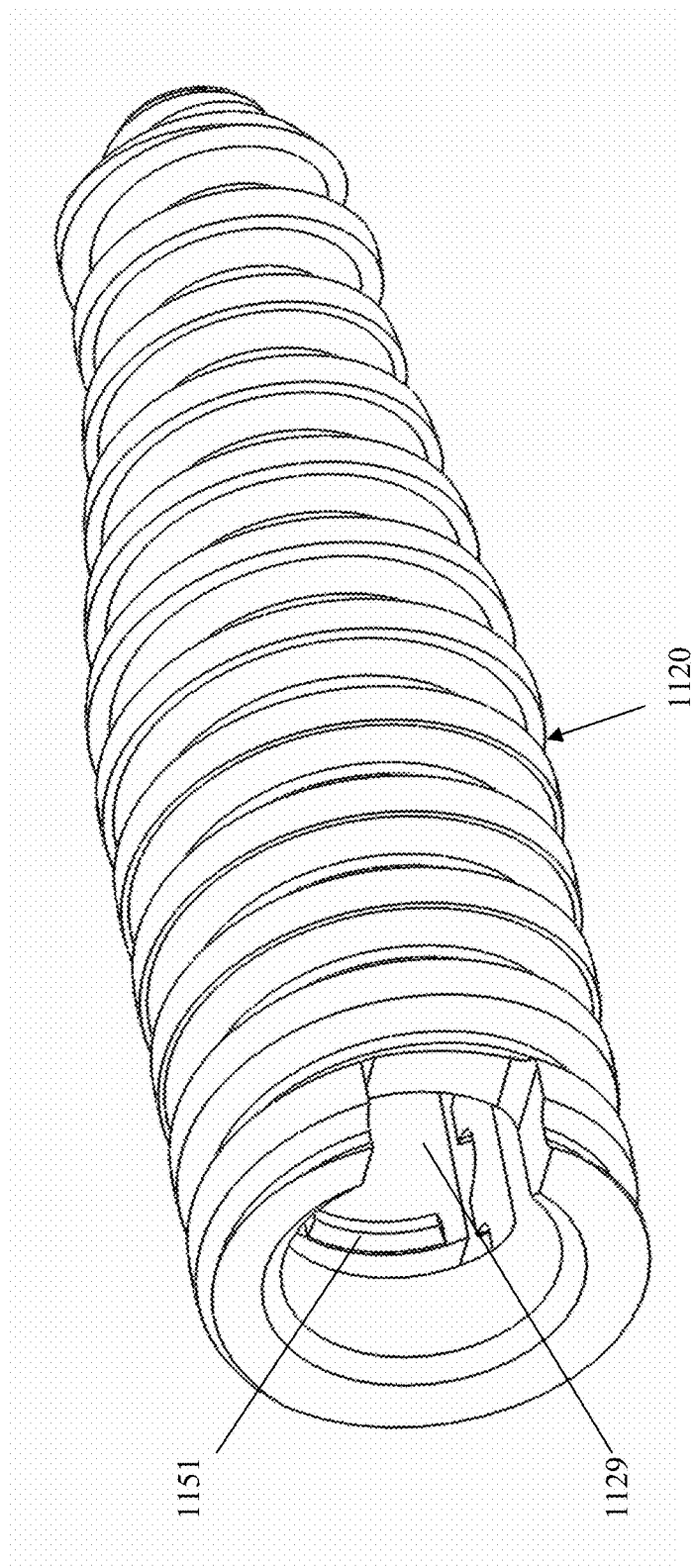
FIG. 18 illustrates a perspective view of a female component of a bone fusion device in accordance with an embodiment of the present disclosure.

FIG. 18 illustrates a perspective view of a female component of a bone fusion device in accordance with an embodiment of the present disclosure. FIG. 18 provides a view of integral tab 1510 within cavity 1129 of female component 1120.

Figure 19:
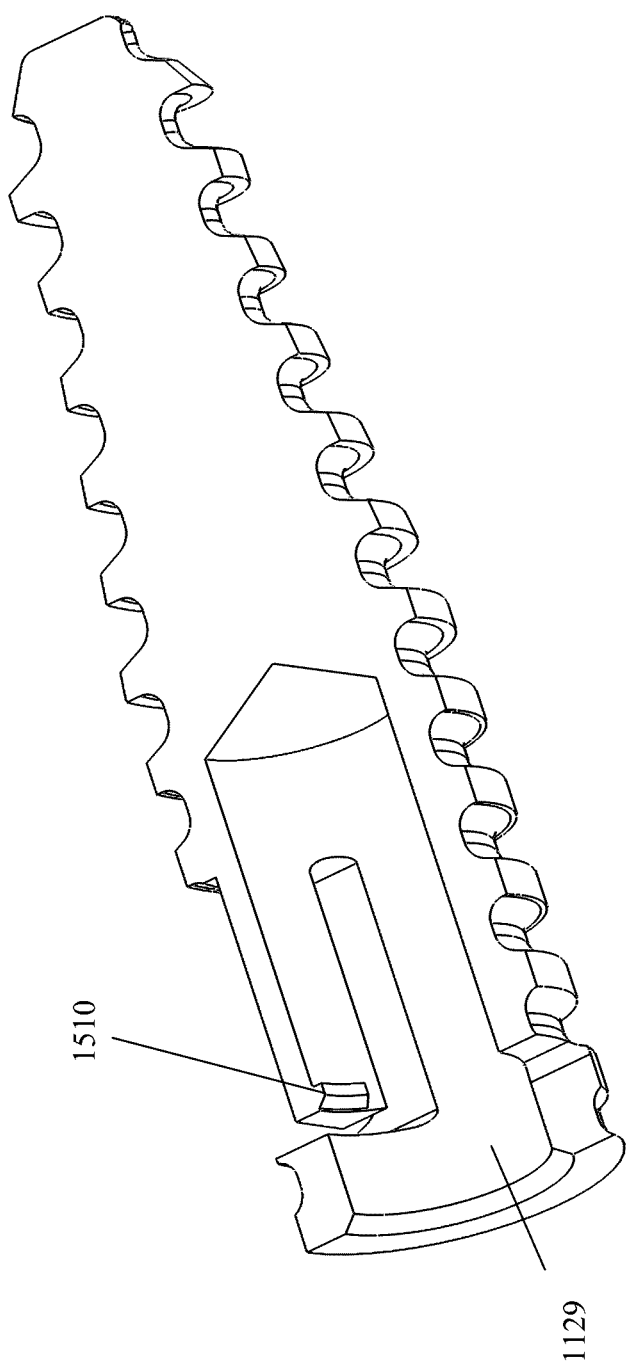
FIG. 19 illustrates a cross-sectional view of a female component of a bone fusion device in accordance with an embodiment of the present disclosure.

FIG. 19 illustrates a cross-sectional view of a female component of a bone fusion device in accordance with an embodiment of the present disclosure. The cross-sectional view provides a view of an inside of cavity 1129, as well as a full view of integral tab 1510 of a reversibly engaging locking mechanism, which is used to hold a connector in place within cavity 1129.

Figure 20:
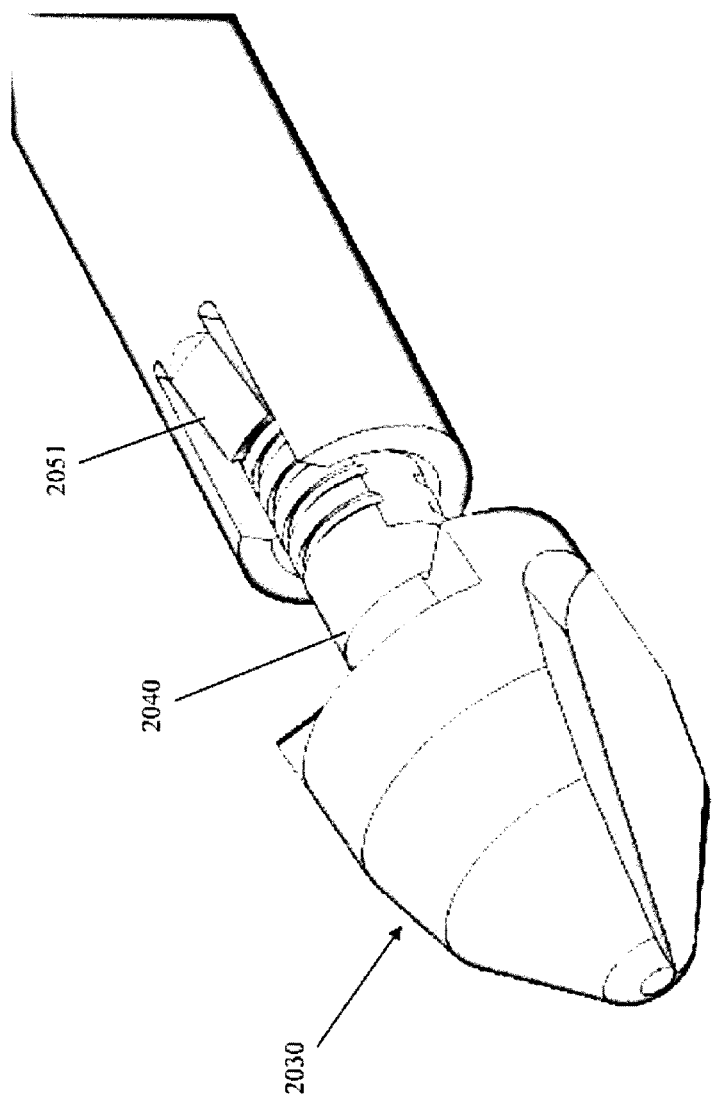
FIG. 20 illustrates another integral deflection means comprising an inline deformed tab of a reversibly engaging locking mechanism for locking with a groove of a connector of a male component in accordance with an embodiment of the present disclosure.

FIG. 20 illustrates another integral deflection means comprising an inline deformed tab of a reversibly engaging locking mechanism for locking with a groove of a connector of a male component in accordance with an embodiment of the present disclosure. Male component 2030 is in a form of a conical shape, with a connector 2040 including a plurality of grooves. Each of the grooves of connector 2040 may engage with a reversibly engaging locking mechanism of a female component 2020 of bone fusion device 2010. Reversibly engaging locking mechanism includes an inline deformed tab 2051 for engaging with grooves of connector 2040. Inline deformed tab 2051 may be bent inwards, and due to a combination of driving slot and tab, may result in easier manufacture.

Figure 21:
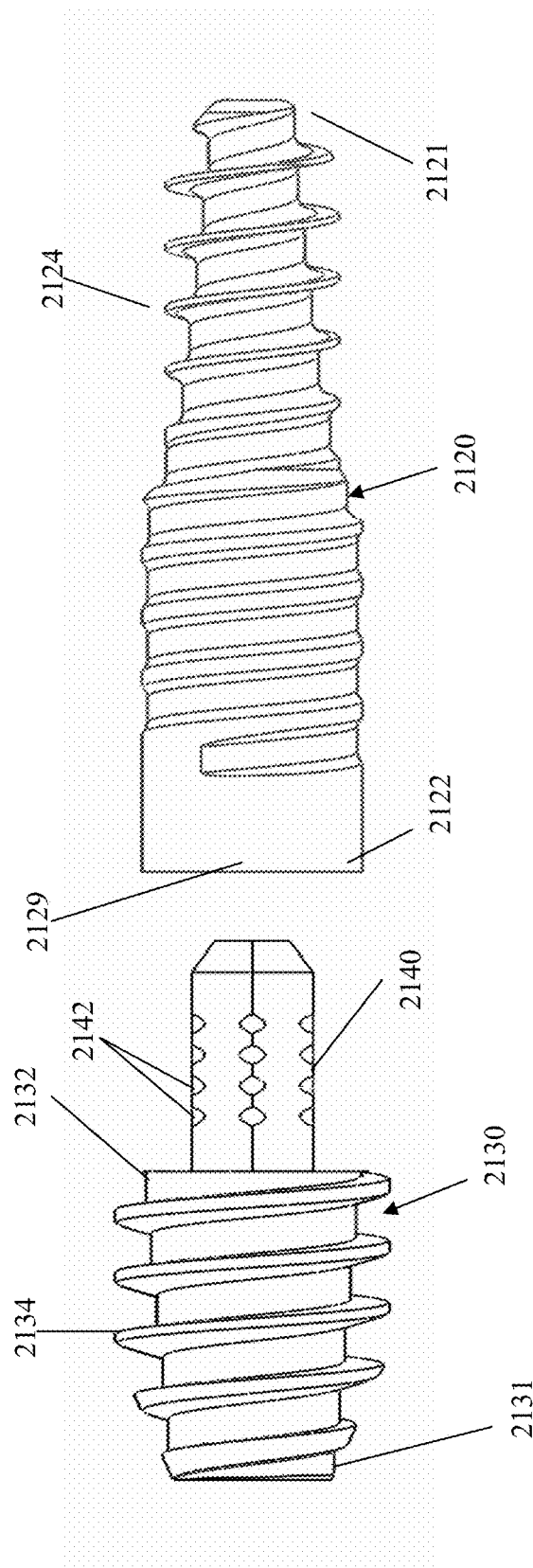
FIG. 21 illustrates a bone fusion device in accordance with an embodiment of the present disclosure.

FIG. 21 illustrates a bone fusion device in accordance with an embodiment of the present disclosure. Bone fusion device 2110 includes a female component 2120 and a male component 2130. Female component 2120 is an elongated stem comprising a first end 2121, a first top 2122, and a cavity 2129. Female component 2120 also includes a spiraling thread 2124 on the exterior, suitable for screwing female component 2120 into a bone or bone piece.

Male component 2130 is an elongated stem comprising a second end 2131 and a second top 2132. Male component 2130 further includes a connector 2140 extending from second top 2132. Male component 2130 also includes a spiraling thread 2134 on the exterior, suitable for screwing male component 2130 into a bone or bone piece.

Female component 2120 and male component 2130 can independently be cylindrical or conical, or any combination thereof. Where the illustrated embodiments show spiraling threads as means to anchor a male component or female component to a bone, alternate anchoring means may be used. Where present, the spiraling threads can be of any type known in the art for screwing into a bone. Thus, in some embodiments, the spiraling thread is a continuous spiraling thread. In other embodiments, the spiraling thread allows self-tapping and/or self-threading.

In an embodiment, the spiraling threads may be continuous. In yet another embodiment, the spiraling threads may spiral in the same direction so that when the device is screwed into opposing bone surfaces and coupled, the opposing pitch of the threads in the bone prevents the device from unscrewing.

The embodiments described herein are not limited to any particular pitch of one rotation of the continuous spiraling thread. For example, the pitch may be 5 mm or greater, 4 mm, 3 mm, 2 mm, 1 mm, or any distance in between the aforementioned distances.

Connector 2140, as shown in FIG. 21, may comprise a plurality of notches 2142 for interlocking with a reversibly engaging locking mechanism of female component 2120. The reversibly engaging locking mechanism may include a ring that can expand to allow insertion of connector 2140. After passing the ring, the notches 2142 may engage with the reversibly engaging locking mechanism which locks connector 2140 of the male component 2130 within the female component 2120 such that the bone pieces that the male component 2130 and the female component 2120 are screwed into become coupled or fused as a bone fusion. Removal of connector 2140 from female component 2120 is facilitated by the ring of the reversibly engaging locking mechanism which acts as a friction axial lock which responds to a predetermined amount of longitudinal force applied to connector 2140 which causes connector 2140 to be removeable or adjustable from within cavity 2129.

Figure 22:
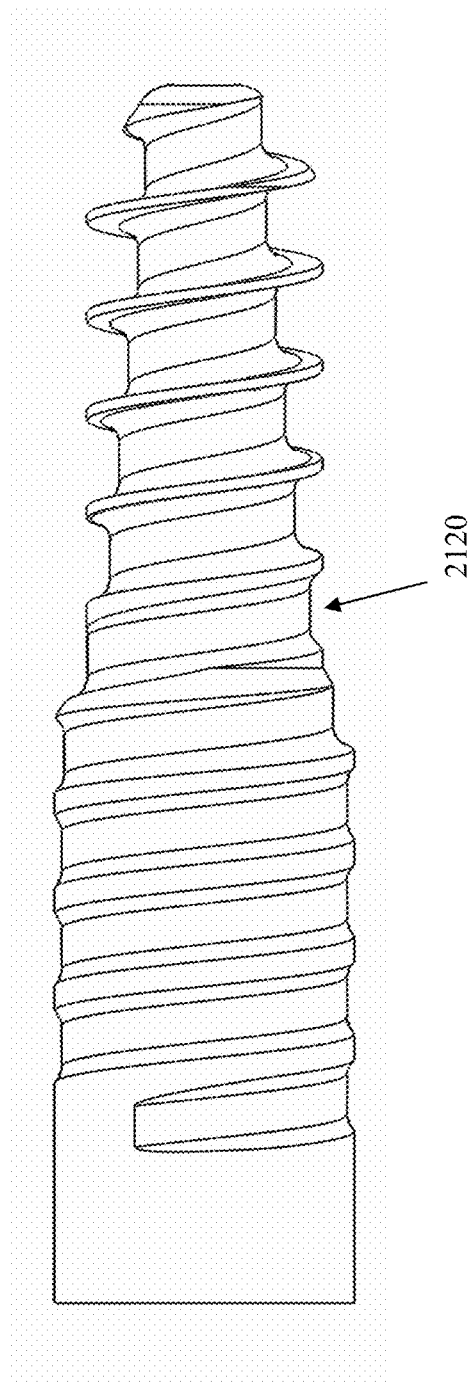
FIG. 22 illustrates a female component of a bone fusion device in accordance with an embodiment of the present disclosure.

FIG. 22 illustrates a female component of a bone fusion device in accordance with an embodiment of the present disclosure. FIG. 22 depicts female component 2120 of an embodiment of the bone fusion device.

Figure 23:
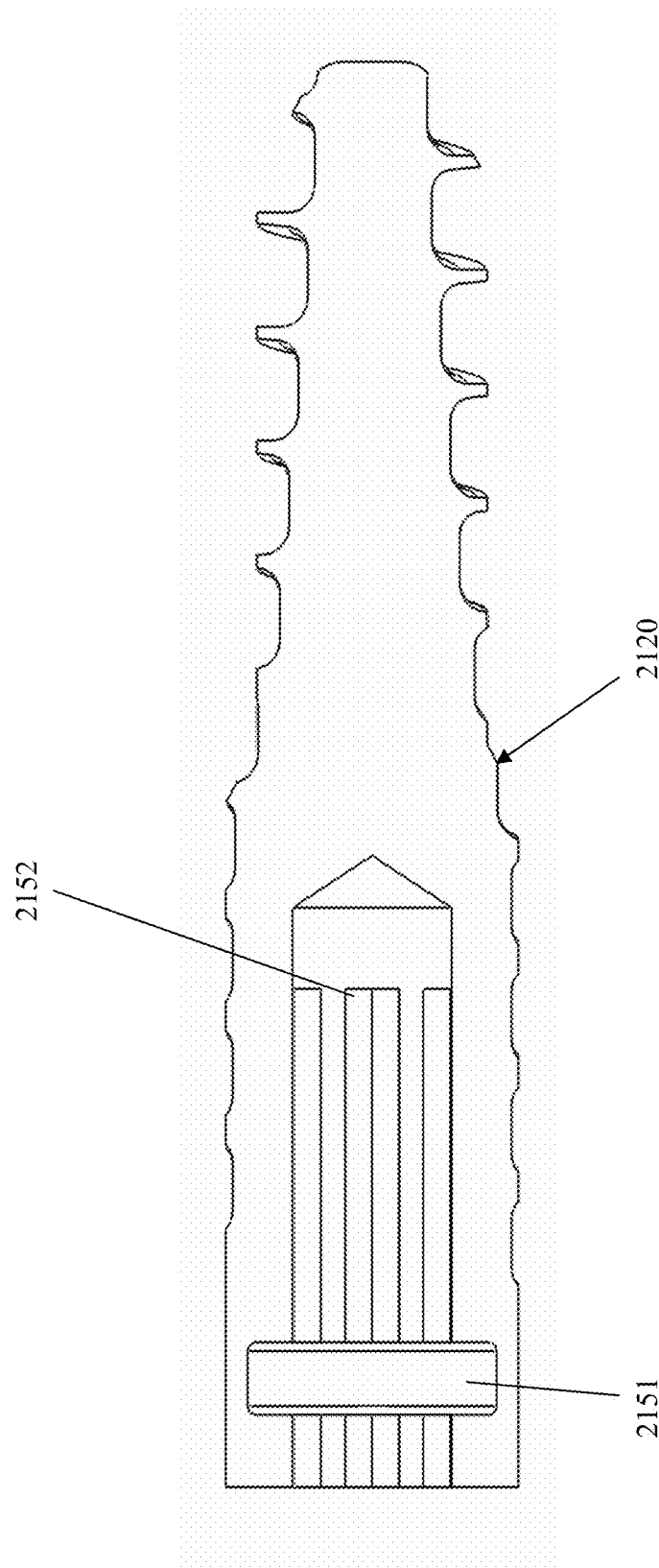
FIG. 23 illustrates a cross-sectional view of a female component of a bone fusion device in accordance with an embodiment of the present disclosure.

FIG. 23 illustrates a cross-sectional view of a female component of a bone fusion device in accordance with an embodiment of the present disclosure. Female component 2120 as illustrated, includes a reversibly engaging locking mechanism. Reversibly engaging locking mechanism resides within cavity 2129 and includes a ring 2151 and a plurality of grooves 2152 for receiving connector 2140. Ring 2151 acts as a friction axial lock which can interact with the notches of connector 2140. This facilitates incremental insertion of connector 2140. Similarly, ring 2151 also supports incremental removal or adjustment of connector 2140. Ring 2151 itself may comprise one or more ridges for catching or engaging with the notches of connector 2140 as connector 2140 is inserted or removed.

Figure 24:
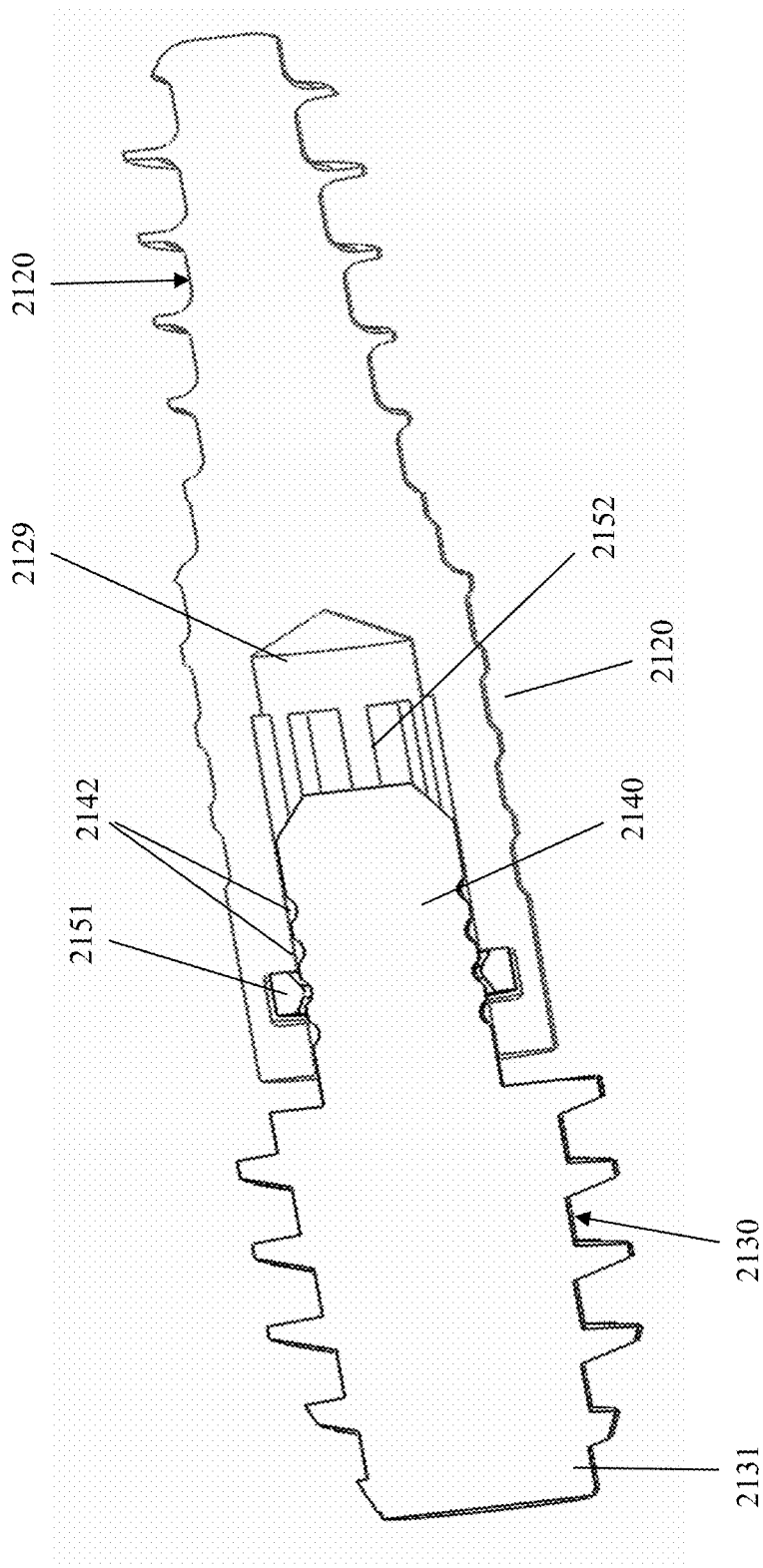
FIG. 24 illustrates a cross-sectional view of a bone fusion device where the male component has been inserted into the female component, in accordance with an embodiment of the present disclosure.

FIG. 24 illustrates a cross-sectional view of a bone fusion device where the male component has been inserted into the female component, in accordance with an embodiment of the present disclosure. As shown, connector 2140 of male component 2130 has been inserted into cavity 2129 of female component 2120. The connector 2140 has engaged with grooves 2152 of the reversibly engaging locking mechanism. Additionally, the notches 2142 of connector 2140 have engaged with ring 2151 and are thus locked in place. Connector 2140 may be inserted longitudinally such that the notches 2142 engage with ring 2151 which acts as a friction axial lock. Increasing amounts of compressive force applied to end 2131 of male component 2130 causes connector 2140 to be implanted deeper within female component 2120. A greater amount of longitudinal force applied outwards would cause removal or outwards movement of connector 2140 in a direction outwards from cavity 2129 in which connector 2140 may be implanted.

Figure 25:
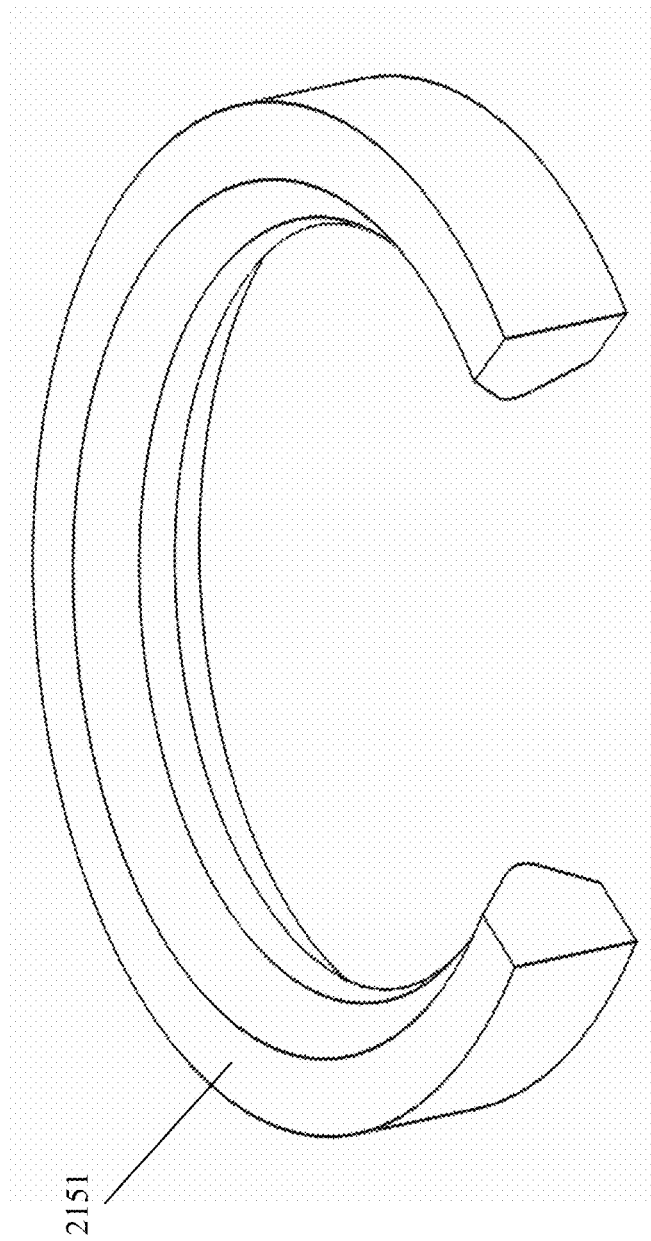
FIG. 25 illustrates an elevated magnified perspective view illustrating a ring, in accordance with an embodiment of the present disclosure.

FIG. 25 illustrates an elevated magnified perspective view illustrating a ring, in accordance with an embodiment of the present disclosure. Ring 2151 is a partial circle with a protruding ridge around its interior surface for engaging the notches of the connector 2140 of FIG. 24. Ring 2151 may be inserted into the cavity 2129 of the female component 2120 at its top 2122, or at an opening in the wall of the female component 2120 similar to the opening shown in FIG. 10.

Figure 26:
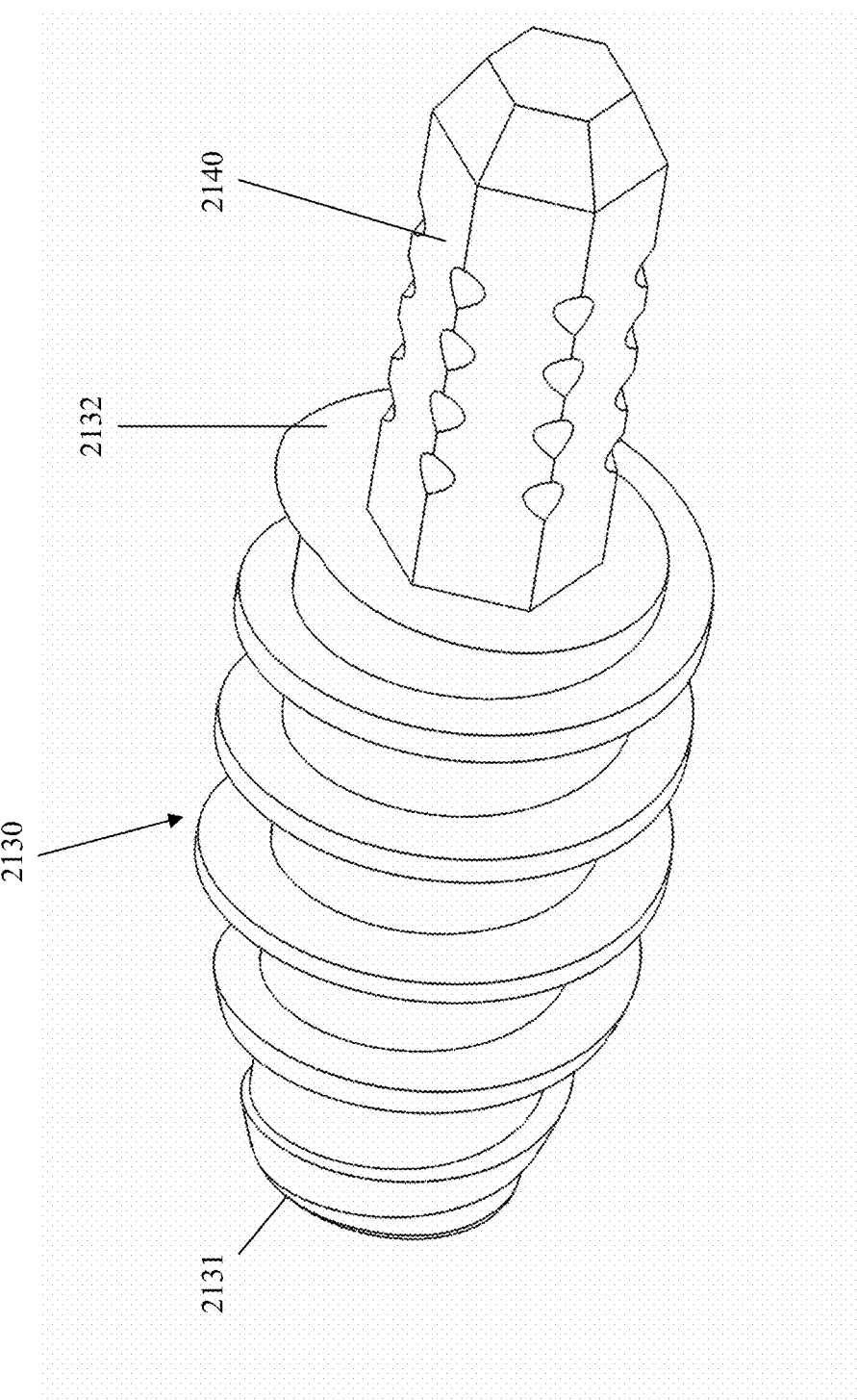
FIG. 26 illustrates an elevated side view perspective illustrating a male component, in accordance with an embodiment of the present disclosure.

FIG. 26 illustrates an elevated side view perspective illustrating a male component, in accordance with an embodiment of the present disclosure. Connector 2140 is hexagonal, with notches for engaging the ring 2151 of FIG. 25, which supports adjustment within, or removal from, female component 2120. Connector 2140's hexagonal shape further provides rotational stability of the male and female components, 2130, 2120, with respect to each other when coupled via the connector 2140.

The foregoing Detailed Description is understood as being in every respect illustrative and exemplary, but not restrictive, and the scope of the embodiments of the present disclosure disclosed herein is not to be determined from the Detailed Description, but rather from the claims as interpreted according to the full breadth permitted by the patent laws. It is understood that the embodiments shown and described herein are only illustrative of the principles of the present disclosure and that various modifications may be implemented by those skilled in the art without departing from the scope and spirit of the present disclosure. Those skilled in the art could implement various other feature combinations without departing from the scope and spirit of the present disclosure.

The invention claimed is:

1. A bone coupling device comprising:
 a female component comprising:
  a first elongated stem portion comprising:
   a first end;
   a first top opposite the first end;
   an opening extending axially within the first elongated stem portion from the first top toward the first end; and
   a locking mechanism forming at least a portion of the opening; and
 a male component comprising:
  a second elongated stem portion comprising:
   a second end; and
   a second top opposite the second end; and
  a connector portion extending from the second top comprising an elongated shaft with a first end and a second end and a plurality of grooves positioned between the first end and the second end, the connector portion being configured to be inserted into the opening in the first elongated stem portion and couple with the locking mechanism of the first component,
 wherein the locking mechanism of the female component comprises a tab configured to mate with at least one of the plurality of grooves of the connector portion when the connector portion is inserted into the opening in the first elongated stem portion to removably fix the female component and the male component.

2. The device of claim 1, wherein the connector portion is integral with the male elongated stem portion.

3. The device of claim 1, wherein the tab of the locking mechanism is integral with the first elongated stem portion of the female component.

4. The device of claim 1, wherein the tab of the locking mechanism is a deformed tab bent inwardly into the opening.

5. The device of claim 1, wherein the tab of the locking mechanism defines a free end with a projection extending inwardly into the opening that is configured to engage at least one of the plurality of grooves of the connector portion when the connector portion is inserted into the opening in the first elongated stem portion.

6. The device of claim 1, wherein an interior surface of the tab forms a portion of the opening of the female component.

7. The device of claim 1, wherein the tab of the locking mechanism of the female component is formed by a partially-separated portion of the first elongated stem portion.

8. The device of claim 7, wherein a first axially elongated gap extends between the tab and an adjacent portion of the first elongated stem portion on a first side of the tab.

9. The device of claim 8, wherein an end gap extends between an axial end of the tab and an adjacent portion of the first elongated stem portion proximate to the first top.

10. The device of claim 9, wherein the first axially elongated gap and the end gap are contiguous.

11. The device of claim 8, wherein a second axially elongated gap extends between the tab and an adjacent portion of the first elongated stem portion on a second side of the tab that opposes the first side.

12. The device of claim 11, wherein the tab defines a free end.

13. The device of claim 12, wherein the free end of the tab is positioned between the first end and the first top.

14. The device of claim 13, wherein the tab is bent inwardly into the opening.

15. The device of claim 1, wherein the opening is cylindrical at least at the first top.

16. The device of claim 1, wherein the opening is substantially cylindrical.

17. The device of claim 1, wherein the connector portion is substantially cylindrical.

18. The device of claim 1, wherein the female component is of one-piece construction.

19. The device of claim 18, wherein the male component is of one-piece construction.

20. The device of claim 1, wherein the locking mechanism is a reversibly engaging locking mechanism such that the connector portion is capable of unlocking from the first elongated stem portion and being removed from the opening.

21. The device of claim 1, wherein the connector portion is substantially solid.

22. A reversible bone coupling device comprising:
 a female component comprising:
  a first elongated stem portion comprising:
   a first end; and
   a first top opposite the first end;
   an opening within the first elongated stem portion extending axially from the first top toward the first end; and
   an engaging locking mechanism forming at least a portion of the opening, the locking mechanism comprising a tab extending partially into the opening; and
 a male component comprising:
  a second elongated stem portion comprising:
   a second end; and
   a second top opposite the second end; and
  a connector portion extending from the second top configured to be inserted into the opening in the first elongated stem portion, the connector comprising an elongated shaft with a first end, a second end, a plurality of axially-spaced grooves partially circumscribing the elongated shaft, and at least one axially-extending substantially smooth surface portion positioned between ends of the grooves,
 wherein the tab mates with at least one of the plurality of grooves of the connector portion to couple the female component and the male component when the connector portion is inserted into the opening and the female and male components are oriented at a first relative orientation, and
 wherein the tab mates with the axially-extending substantially smooth surface portion of the connector portion to allow decoupling of the female component and the male component when the connector portion is inserted into the opening and the female and male components are oriented at a second relative orientation that differs from the first relative orientation.

* * * * *